(12) United States Patent
Jacquot et al.

(10) Patent No.: US 9,821,072 B2
(45) Date of Patent: Nov. 21, 2017

(54) ACTIVATED NEUROTENSIN MOLECULES AND THE USES THEREOF

(71) Applicants: VECT-HORUS, Marseilles (FR); CENTRE NATIONAL DE LA RECHERCHE SCIENTIFIQUE, Paris (FR)

(72) Inventors: Guillaume Jacquot, Beaurecueil (FR); Pascaline Lecorche, Marseilles (FR); Michel Khrestchatisky, Marseilles (FR)

(73) Assignees: VECT-HORUS, Marseille (FR); CENTRE NATIONAL DE LA RECHERCHE SCIENTIFIQUE, Paris (FR)

(*) Notice: Subject to any disclaimer, the term of this patent is extended or adjusted under 35 U.S.C. 154(b) by 0 days.

(21) Appl. No.: 15/111,835

(22) PCT Filed: Jan. 19, 2015

(86) PCT No.: PCT/EP2015/050856
§ 371 (c)(1),
(2) Date: Jul. 15, 2016

(87) PCT Pub. No.: WO2015/107182
PCT Pub. Date: Jul. 23, 2015

(65) Prior Publication Data
US 2016/0354480 A1  Dec. 8, 2016

(30) Foreign Application Priority Data
Jan. 20, 2014 (EP) ..................... 14305074

(51) Int. Cl.
| C07K 7/08 | (2006.01) |
| C07K 7/06 | (2006.01) |
| A61K 38/10 | (2006.01) |
| A61K 38/08 | (2006.01) |
| A61P 25/08 | (2006.01) |
| A61P 25/00 | (2006.01) |
| A61P 9/00 | (2006.01) |
| A61K 47/48 | (2006.01) |
| A61K 38/00 | (2006.01) |

(52) U.S. Cl.
CPC ........ *A61K 47/48246* (2013.01); *A61K 38/08* (2013.01); *A61K 38/10* (2013.01); *C07K 7/06* (2013.01); *C07K 7/083* (2013.01); *A61K 38/00* (2013.01)

(58) Field of Classification Search
None
See application file for complete search history.

(56) References Cited

U.S. PATENT DOCUMENTS

| 8,729,029 B2 | 5/2014 | Khrestchatisky et al. |
| 8,877,716 B2 | 11/2014 | Vlieghe et al. |
| 9,328,143 B2 | 5/2016 | Khrestchatisky et al. |
| 2011/0230416 A1 | 9/2011 | Khrestchatisky et al. |
| 2013/0108548 A1 | 5/2013 | Vlieghe et al. |

FOREIGN PATENT DOCUMENTS

| WO | WO 2010/046588 | 4/2010 |
| WO | WO 2011/131896 | 10/2011 |
| WO | WO 2012/000118 | 1/2012 |

OTHER PUBLICATIONS

Zhang, L. et al. "Synthesis and Applications of Polyamine Amino Acid Residues: Improving the Bioactivity of an Analgesic Neuropeptide, Neurotensin" *Journal of Medicinal Chemistry*, Mar. 26, 2009, pp. 1514-1517, vol. 52, No. 6.
Written Opinion in International Application No. PCT/EP2015/050856, dated Apr. 17, 2015, pp. 1-6.

*Primary Examiner* — Zachary Howard
(74) *Attorney, Agent, or Firm* — Saliwanchik, Lloyd & Eisenschenk

(57) ABSTRACT

The present invention relates to activated neurotensin, pharmaceutical compositions comprising the same, and the uses thereof. The compounds and compositions of the invention may be used, e.g., to reduce body temperature, attenuate or halt seizures, reduce excitotoxicity, promote neuroprotection, reduce neuroinflammation and aberrant axonal sprouting or reduce pain.

7 Claims, 16 Drawing Sheets

Figure 1:
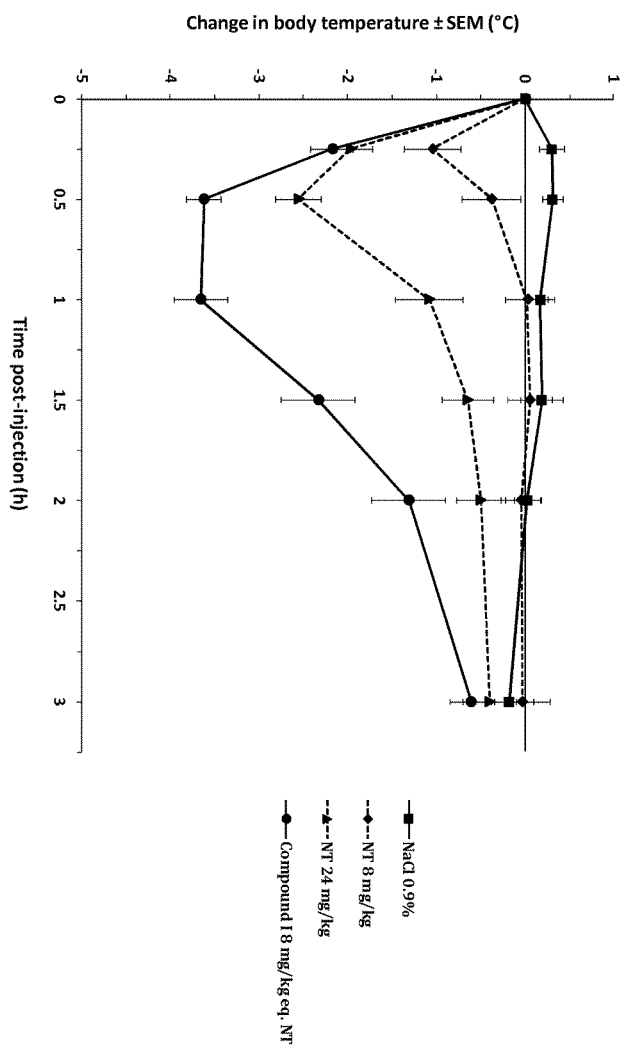

A : ANOVA + post hoc Dunnett test; ***P<0,001

B: ANOVA + post hoc Tukey test; *compared to SE group; #compared to SE30 + Compound XIV group; +compared to DZP group. p<0,05; pp<0,01; pop<0,001

A

B

A

B

```
SEQUENCE LISTING

<160> NUMBER OF SEQ ID NOS: 11

<210> SEQ ID NO 1
<211> LENGTH: 13
<212> TYPE: PRT
<213> ORGANISM: homo sapiens
<220> FEATURE:
<221> NAME/KEY: MISC_FEATURE
<222> LOCATION: (1)..(1)
<223> OTHER INFORMATION: amino acid is pE

<400> SEQUENCE: 1

Glu Leu Tyr Glu Asn Lys Pro Arg Arg Pro Tyr Ile Leu
1               5                   10

<210> SEQ ID NO 2
<211> LENGTH: 6
<212> TYPE: PRT
<213> ORGANISM: Artificial
<220> FEATURE:
<223> OTHER INFORMATION: amino acids 8-13 of human neurotensin

<400> SEQUENCE: 2

Arg Arg Pro Tyr Ile Leu
1               5

<210> SEQ ID NO 3
<211> LENGTH: 8
<212> TYPE: PRT
<213> ORGANISM: Artificial
<220> FEATURE:
<223> OTHER INFORMATION: amino acids 6-13 of human neurotensin

<400> SEQUENCE: 3

Lys Pro Arg Arg Pro Tyr Ile Leu
1               5

<210> SEQ ID NO 4
<211> LENGTH: 12
<212> TYPE: PRT
<213> ORGANISM: Artificial
<220> FEATURE:
<223> OTHER INFORMATION: amino acids 2-13 of human neurotensin

<400> SEQUENCE: 4
```

```
Leu Tyr Glu Asn Lys Pro Arg Arg Pro Tyr Ile Leu
1               5                   10

<210> SEQ ID NO 5
<211> LENGTH: 5
<212> TYPE: PRT
<213> ORGANISM: Artificial
<220> FEATURE:
<223> OTHER INFORMATION: activator group

<400> SEQUENCE: 5

Met Pro Arg Leu Arg
1               5

<210> SEQ ID NO 6
<211> LENGTH: 5
<212> TYPE: PRT
<213> ORGANISM: Artificial
<220> FEATURE:
<223> OTHER INFORMATION: activator group
<220> FEATURE:
<221> NAME/KEY: MISC_FEATURE
<222> LOCATION: (2)..(2)
<223> OTHER INFORMATION: X is Pip

<400> SEQUENCE: 6

Met Xaa Arg Leu Arg
1               5

<210> SEQ ID NO 7
<211> LENGTH: 5
<212> TYPE: PRT
<213> ORGANISM: Artificial
<220> FEATURE:
<223> OTHER INFORMATION: activator group
<220> FEATURE:
<221> NAME/KEY: MISC_FEATURE
<222> LOCATION: (2)..(2)
<223> OTHER INFORMATION: X is Thz

<400> SEQUENCE: 7

Met Xaa Arg Leu Arg
1               5

<210> SEQ ID NO 8
<211> LENGTH: 8
<212> TYPE: PRT
<213> ORGANISM: Artificial
<220> FEATURE:
<223> OTHER INFORMATION: activator group
<220> FEATURE:
<221> NAME/KEY: MISC_FEATURE
<222> LOCATION: (1)..(1)
<223> OTHER INFORMATION: C is a D-Cys

<400> SEQUENCE: 8

Cys Met Pro Arg Leu Arg Gly Cys
1               5

<210> SEQ ID NO 9
<211> LENGTH: 8
<212> TYPE: PRT
<213> ORGANISM: Artificial
<220> FEATURE:
<223> OTHER INFORMATION: activator group
<220> FEATURE:
<221> NAME/KEY: MISC_FEATURE
<222> LOCATION: (1)..(1)
<223> OTHER INFORMATION: C is a D-Cys
<220> FEATURE:
```

```
<221> NAME/KEY: MISC_FEATURE
<222> LOCATION: (3)..(3)
<223> OTHER INFORMATION: X is Pip
<220> FEATURE:
<221> NAME/KEY: MISC_FEATURE
<222> LOCATION: (7)..(7)
<223> OTHER INFORMATION: X is Sar

<400> SEQUENCE: 9

Cys Met Xaa Arg Leu Arg Xaa Cys
1               5

<210> SEQ ID NO 10
<211> LENGTH: 8
<212> TYPE: PRT
<213> ORGANISM: Artificial
<220> FEATURE:
<223> OTHER INFORMATION: activator group
<220> FEATURE:
<221> NAME/KEY: MISC_FEATURE
<222> LOCATION: (1)..(1)
<223> OTHER INFORMATION: C is a D-Cys
<220> FEATURE:
<221> NAME/KEY: MISC_FEATURE
<222> LOCATION: (3)..(3)
<223> OTHER INFORMATION: X is Thz
<220> FEATURE:
<221> NAME/KEY: MISC_FEATURE
<222> LOCATION: (8)..(8)
<223> OTHER INFORMATION: X is Pen

<400> SEQUENCE: 10

Cys Met Xaa Arg Leu Arg Gly Xaa
1               5

<210> SEQ ID NO 11
<211> LENGTH: 8
<212> TYPE: PRT
<213> ORGANISM: Artificial
<220> FEATURE:
<223> OTHER INFORMATION: activator group
<220> FEATURE:
<221> NAME/KEY: MISC_FEATURE
<222> LOCATION: (1)..(1)
<223> OTHER INFORMATION: C is a D-Cys
<220> FEATURE:
<221> NAME/KEY: MISC_FEATURE
<222> LOCATION: (3)..(3)
<223> OTHER INFORMATION: X is Pip
<220> FEATURE:
<221> NAME/KEY: MISC_FEATURE
<222> LOCATION: (7)..(7)
<223> OTHER INFORMATION: X is Sar
<220> FEATURE:
<221> NAME/KEY: MISC_FEATURE
<222> LOCATION: (8)..(8)
<223> OTHER INFORMATION: X is Pen

<400> SEQUENCE: 11

Cys Met Xaa Arg Leu Arg Xaa Xaa
1               5
```

ACTIVATED NEUROTENSIN MOLECULES AND THE USES THEREOF

CROSS-REFERENCE TO RELATED APPLICATION

This application is the U.S. national stage application of International Patent Application No. PCT/EP2015/050856, filed Jan. 19, 2015.

The present invention relates to novel compounds comprising neurotensin or an analog thereof conjugated to an activator group (also termed "activated neurotensin"), pharmaceutical compositions comprising the same, and the uses thereof. The compounds and compositions of the invention may be used to reduce body temperature (for instance, to induce controlled pharmacological normo- or hypothermia) in mammals in need thereof, particularly to induce neuroprotection. They may particularly be used to reduce central nervous system (CNS) damages associated with, e.g., ischemia, trauma or seizures, as well as to treat pain. The compounds and compositions of the invention may also be used for treating convulsions, hyperthermia, or any condition that could benefit from a biological activity of neurotensin.

BACKGROUND

Reduction of body temperature (hypothermia) is a potent neuroprotective approach against damages occurring in various situations such as brain ischemia associated with stroke, cardiac arrest or neonatal ischemia, seizures, severe traumatic brain and spinal cord injuries, or heart surgeries. Reduction of hyperthermia to normothermia is also warranted in pathological situations with elevated body temperature (such as intracranial hypertension (ICH), ischemic or hemorrhagic stroke, traumatic brain injury (TBI), sepsis or any viral, bacterial or parasitic infection associated with fever).

Physical approaches for reducing body temperature have been employed in the art which involve either external methods, such as cooling material or treatment (e.g., cooling blankets, ice baths, etc.) or internal methods (e.g., cooling probes, infusion of cold fluids, etc.), or both. These physical approaches, however, are difficult to implement, expensive, may have delayed onset of action and/or transient effect, and may induce undesirable side effects such as shivering that necessitate administration of additional treatments, including paralytic or sedative agents.

Pharmacological approaches have been suggested, which essentially use neurotensin or analogs thereof. Neurotensin (NT) is a linear tridecapeptide with the amino acid sequence pyroGlu-Leu-Tyr-Glu-Asn-Lys-Pro-Arg-Arg-Pro-Tyr-Ile-Leu-OH. In mammals endogenous NT is mainly expressed in the CNS where it acts as a neurotransmitter and neuromodulator interacting with dopaminergic systems. NT is also expressed in peripheral tissues, mainly in the gastrointestinal tract, where it plays a role in gut motility. In addition, deregulation of the NT system has been implicated in the pathophysiology of many neuropsychiatric diseases as well as several cancers. When administered directly into the brain or the spinal cord, NT exerts a potent µ-independent antinociceptive effect and hypothermia. Although clinical use of NT could provide an interesting and innovative means to treat many pathophysiological conditions, it is hampered by a very rapid proteolytic cleavage in plasma upon systemic administration. Moreover its poor blood-brain barrier (BBB) permeability hampers its therapeutic potential, unless administered directly into the brain or the spinal cord. Therefore, medicinal chemistry methods allowing the design of neurotensin-based compounds able to elicit central activity upon systemic administration are needed. It has been proposed to either design neurotensin analogs and/or to conjugate neurotensin or its analogs to delivery agents such as antibodies (WO2011/127580) or transport peptides (WO2010/063122).

However, there is a need in the art for neurotensin-based pharmacological agents with improved efficacy and safety profiles, including a rapid onset of action and a biological activity in different pathophysiological conditions, including hyperthermia, excitotoxic processes, neuroinflammation, and convulsions, as well as pain.

SUMMARY OF THE INVENTION

The present invention discloses novel neurotensin compounds having improved therapeutic properties, and their use in mammals, particularly human subjects. The invention is based on the design of novel molecules comprising (a) NT or an analog thereof covalently coupled to (b) an activator group. The "activated NT" compounds of the invention have enhanced BBB permeability and resistance to proteolytic cleavage, and demonstrate highly improved biological activity. In particular, upon systemic administration, the activated NT compounds of the invention induce remarkable therapeutic effects in vivo, including hypothermia in various therapeutic conditions, anti-convulsant effects in status epilepticus, and neuroprotective and anti-neuroinflammatory effects. Importantly, the compounds of the present invention exhibit strong biological activity with very rapid onset of action, together with a relatively short duration of action and very good safety profile. These properties provide very good pharmacodynamic and safety prerequisites for a fine control and tuning of the biological effect in acute conditions requiring safe therapeutic interventions. Moreover, the compounds of the invention retain some activity upon repeated administration, and thus can be used for repeated or sub-chronic treatment.

An object of the invention therefore relates to a compound comprising a neurotensin polypeptide covalently coupled to an activator group. The activator group comprises the amino acid sequence M-aa1-R-L-R, wherein aa1 is Proline or an analog thereof. Coupling to the NT polypeptide may be direct or indirect, i.e., through a linker group.

A further object of the invention relates to a pharmaceutical composition comprising a compound as defined above and a pharmaceutically acceptable carrier or excipient.

Another object of the invention is a method of making a compound as defined above, comprising covalent coupling of a neurotensin polypeptide to an activator group as defined above, preferably through indirect covalent coupling using a linker group.

A further object of the invention concerns the use of a compound or composition as defined above as a medicament. The compounds or compositions may be used to reduce body temperature (e.g., to induce hypothermia or normothermia) in a mammalian subject, or to induce neuroprotection (e.g., to reduce brain damage), as well as to treat pain.

A further object of the invention concerns the use of a compound or composition as defined above for treating a subject having brain damage.

A further aspect of the invention relates to a method of inducing hypothermia in a mammalian subject, comprising the systemic administration to said subject of a compound or composition as defined above.

A further object of the invention is a method of treating a subject having brain damage, comprising the systemic administration to said subject of a compound or composition as defined above.

The invention may be used to treat (e.g., protect, prevent, or reduce the effect of) brain damage in any mammalian subject, such as a human patient. It is particularly suited for treating a subject having cerebral ischemia, stroke, cardiac arrest or neonatal ischemia, seizures, severe traumatic head and spinal cord injury, heart surgery, ICH, sepsis or any viral, bacterial or parasitic infection associated with fever. It is also suited for treating a subject having seizures resistant to standard anticonvulsant agents or hyperthermia that is resistant to standard antipyretic pharmacological agents or in combination with standard cooling techniques to initiate patient cooling more quickly.

LEGEND TO THE FIGURES

FIG. 1. Effect of saline (NaCl 0.9%), NT or compound I on rectal body temperature of Swiss (CD-1) mice following intravenous injection (bolus) at the NT molar equivalent (eq.) dose of 8 mg/kg.

Figure 2:
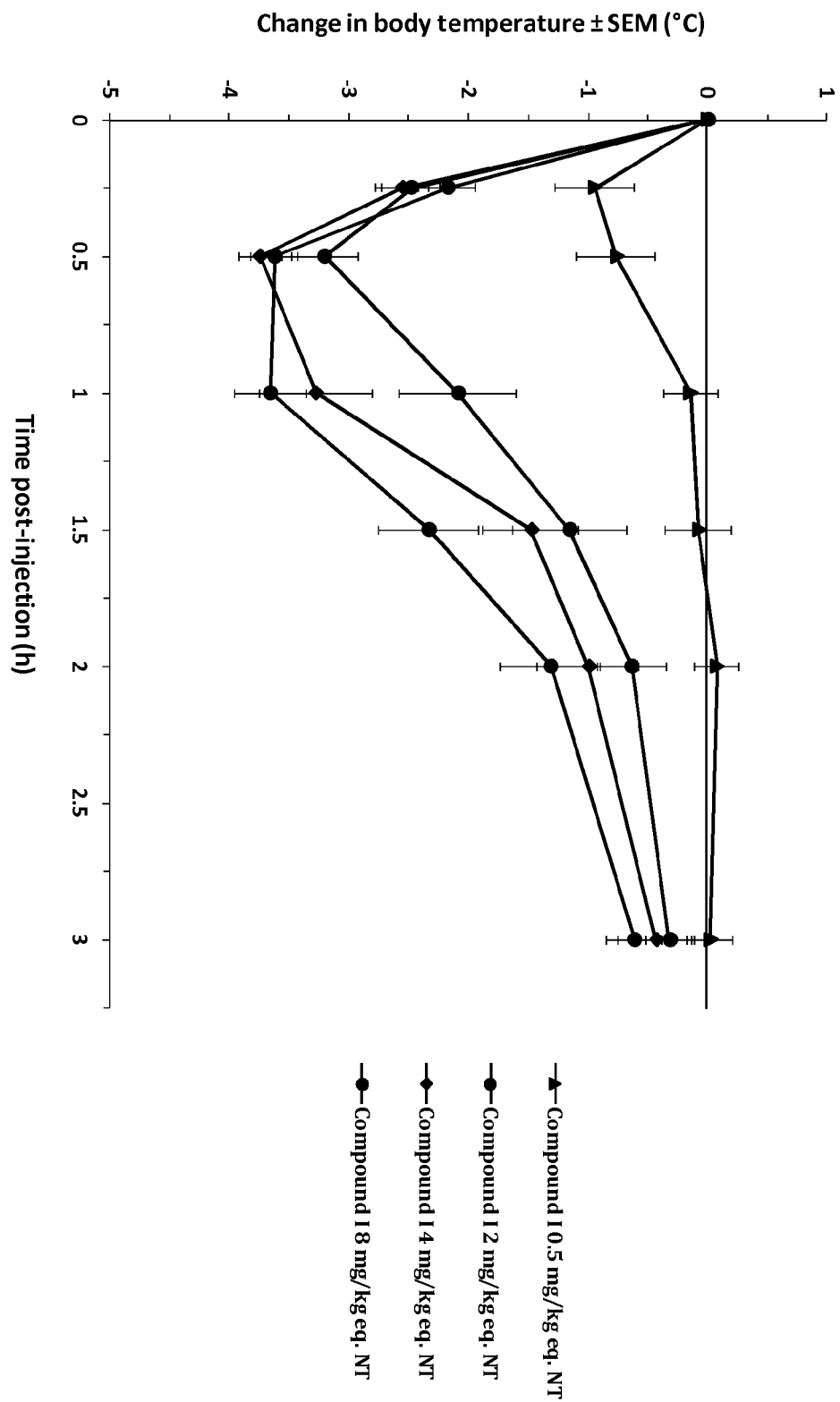

FIG. 2. Hypothermic dose-response relationship of compound I in Swiss (CD-1) mice injected i.v. (bolus) at NT eq. doses ranging from 0.5 to 8 mg/kg.

Figure 3:
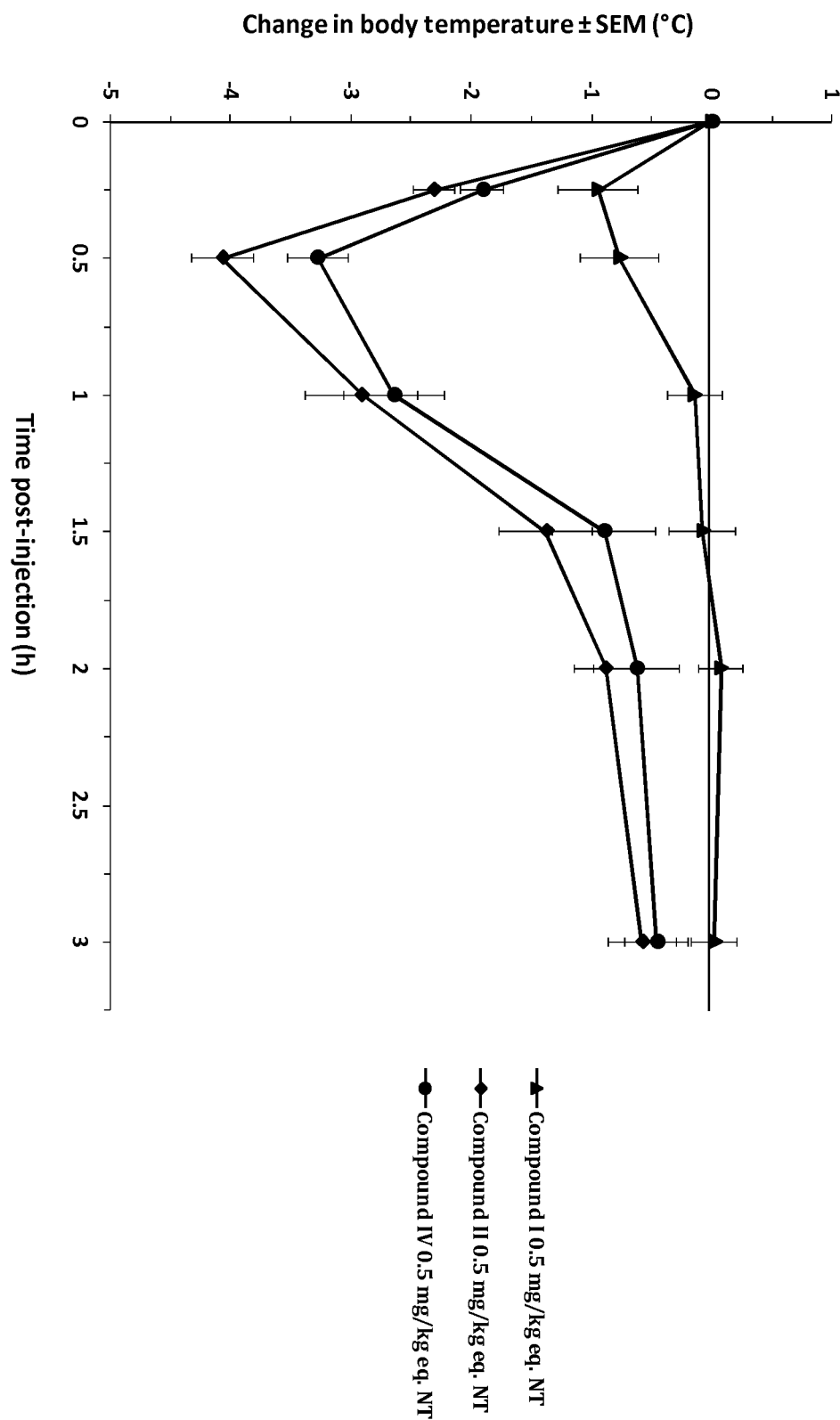

FIG. 3. Hypothermic response in Swiss (CD-1) mice of compound I, compound II and compound IV. Compounds I, II and IV were injected i.v. (bolus) in mice at the same dose level of 0.5 mg/kg eq. NT.

Figure 4:
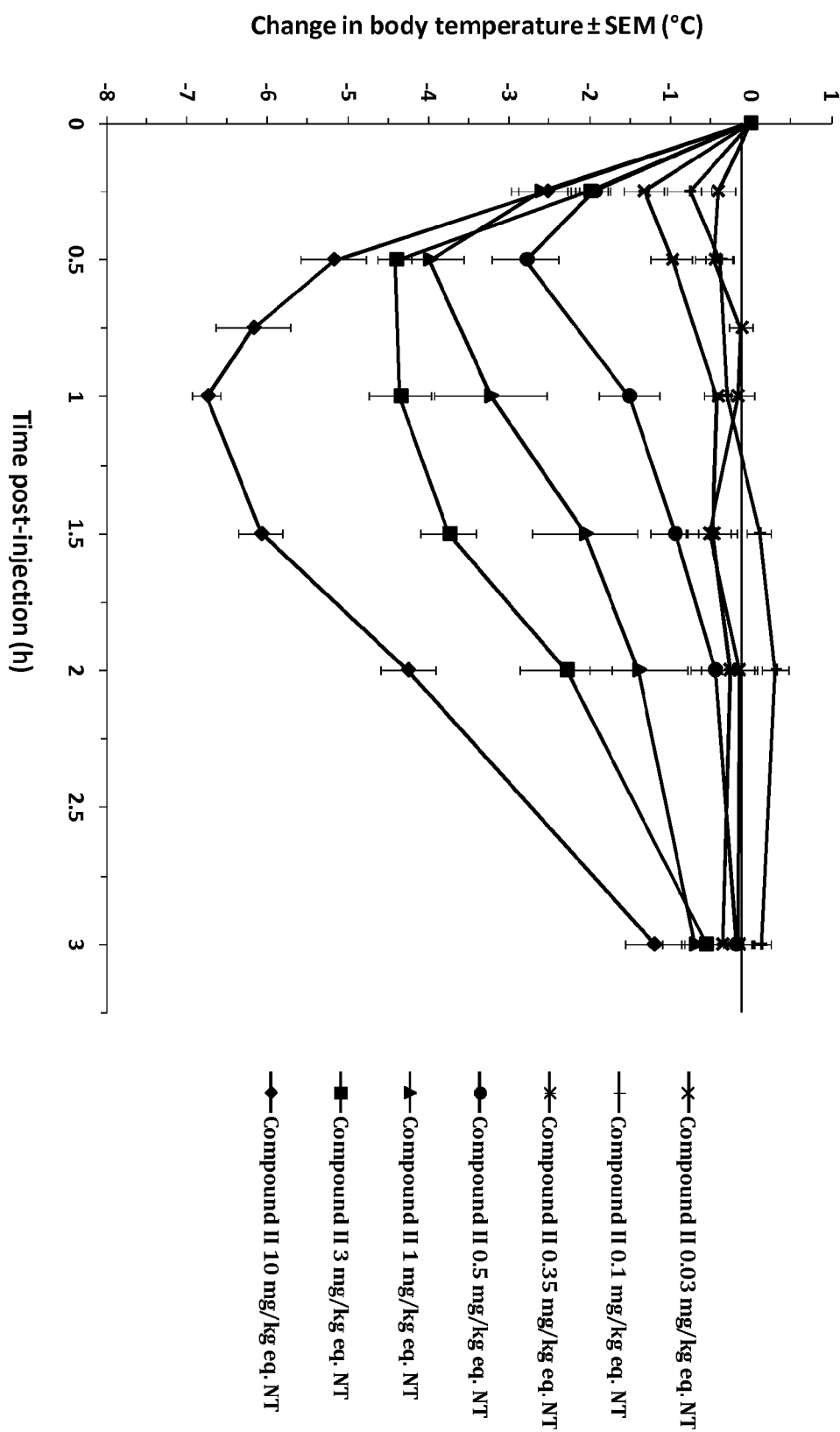

FIG. 4. Hypothermic dose-response relationship of compound II in Swiss (CD-1) mice injected i.v. (bolus) at NT eq. doses ranging from 0.03 to 10 mg/kg. The minimal effective dose (MED) was 0.35 mg/kg eq. NT and the maximal effect was observed at 10 mg/kg eq. NT.

Figure 5:
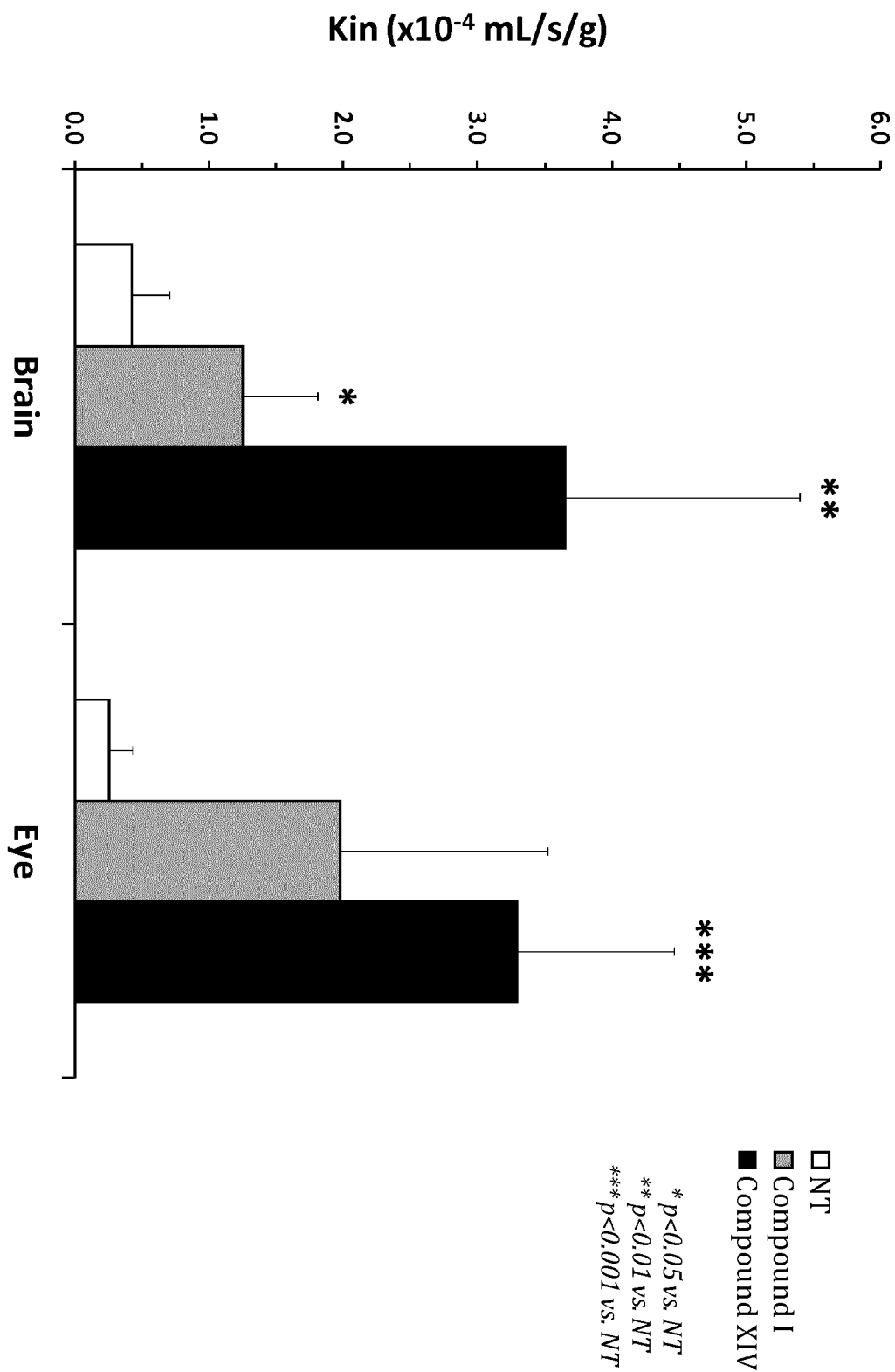

FIG. 5. BBB and blood retina barrier (BRB) transport of [$^3$H-Tyr3]-NT, [$^3$H-Tyr3]-compound I and [$^3$H-Tyr3]-compound XIV in mice using in situ brain perfusion.

Figure 6:
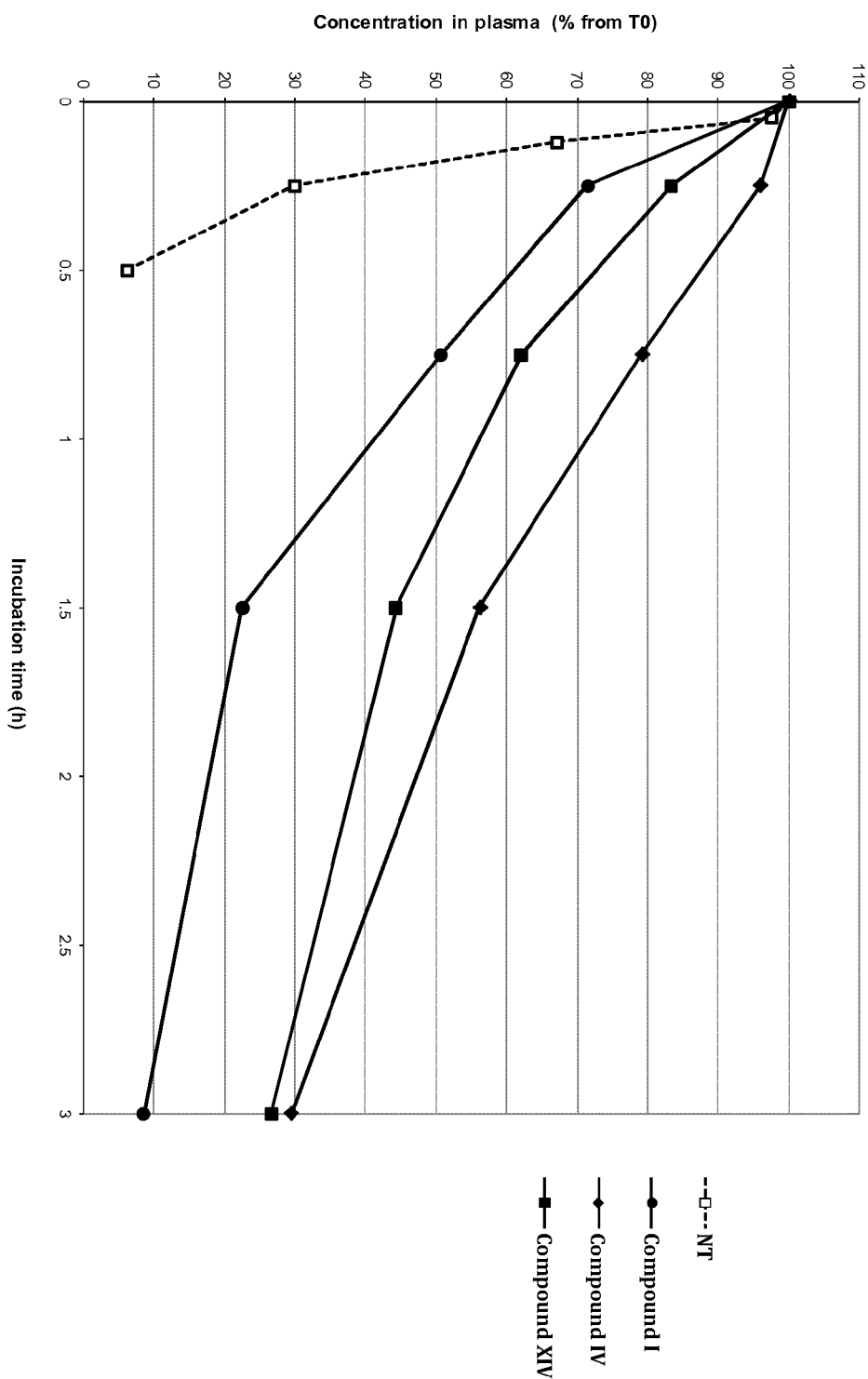

FIG. 6. In vitro blood stability of NT, compound I, compound IV and compound XIV. Peptides were incubated at 37° C. in freshly collected Swiss (CD-1) mouse blood and the percentage of remaining intact peptide was quantified in the plasma fraction at indicated time-points using a liquid chromatography-tandem mass spectrometry (LC-MS/MS) analytical method.

Figure 7:
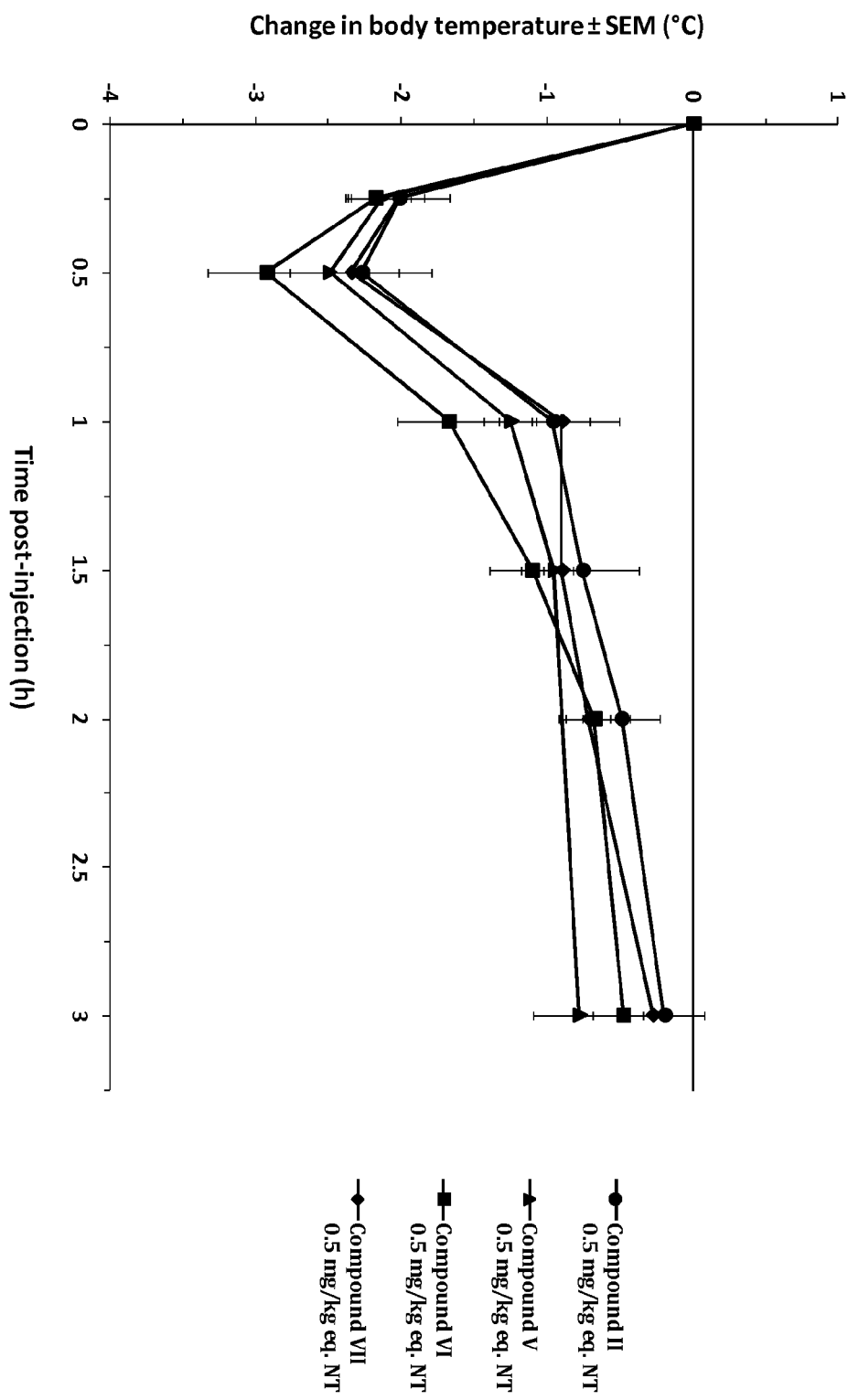

FIG. 7. Comparison of the hypothermic response in Swiss (CD-1) mice of compound II with activated neurotensin compounds of the invention comprising shorter analogs of NT. Compound II, compound V, compound VI or compound VII were injected i.v. (bolus) in mice at the same dose level of 0.5 mg/kg eq. NT. All conjugates showed similar hypothermic potency.

Figure 8:
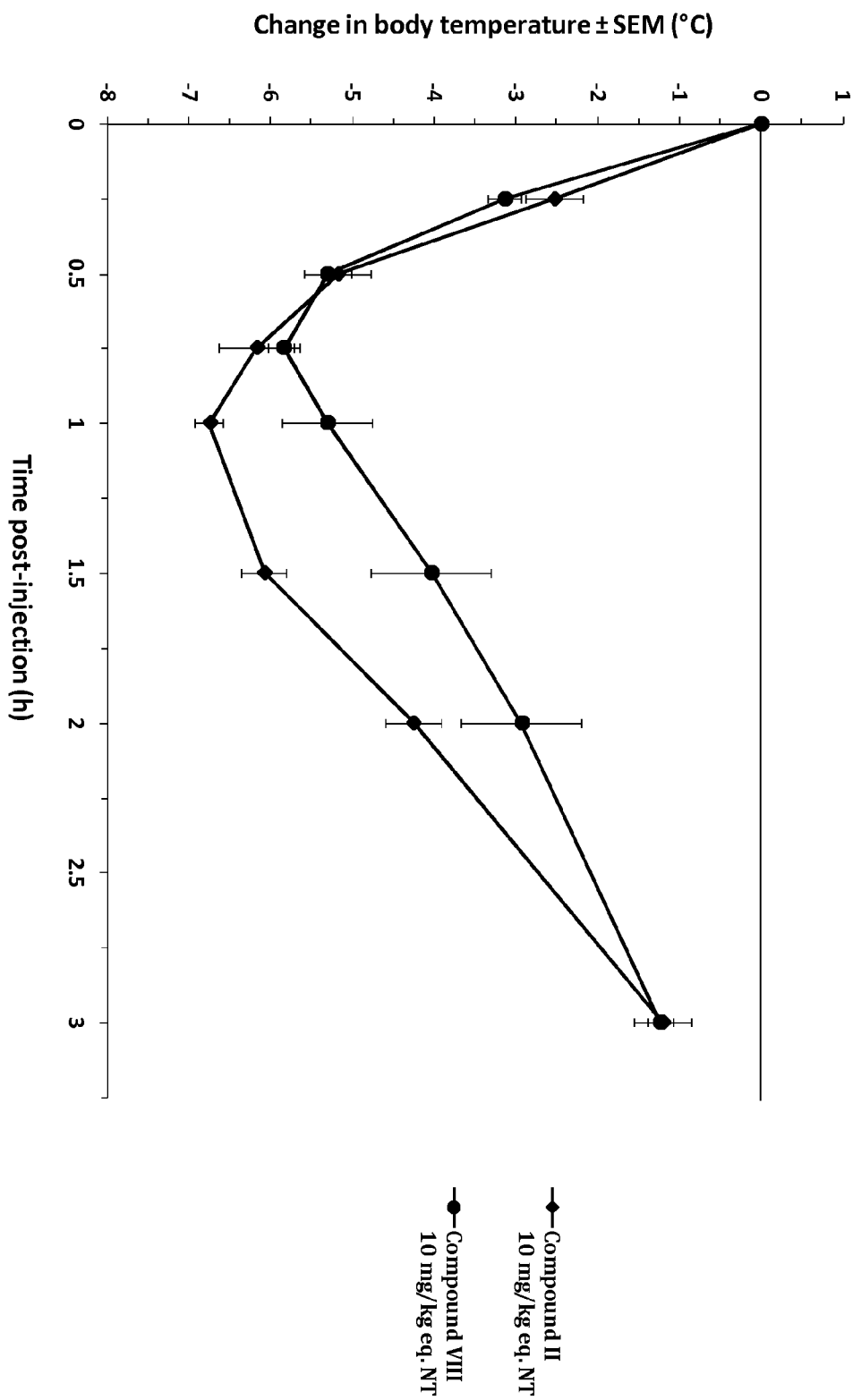

FIG. 8. Hypothermic effect of compounds II and VIII in Swiss (CD-1) mice. Compound II or compound VIII were injected i.v. (bolus) in mice at the same dose level of 10 mg/kg eq. NT.

Figure 9:
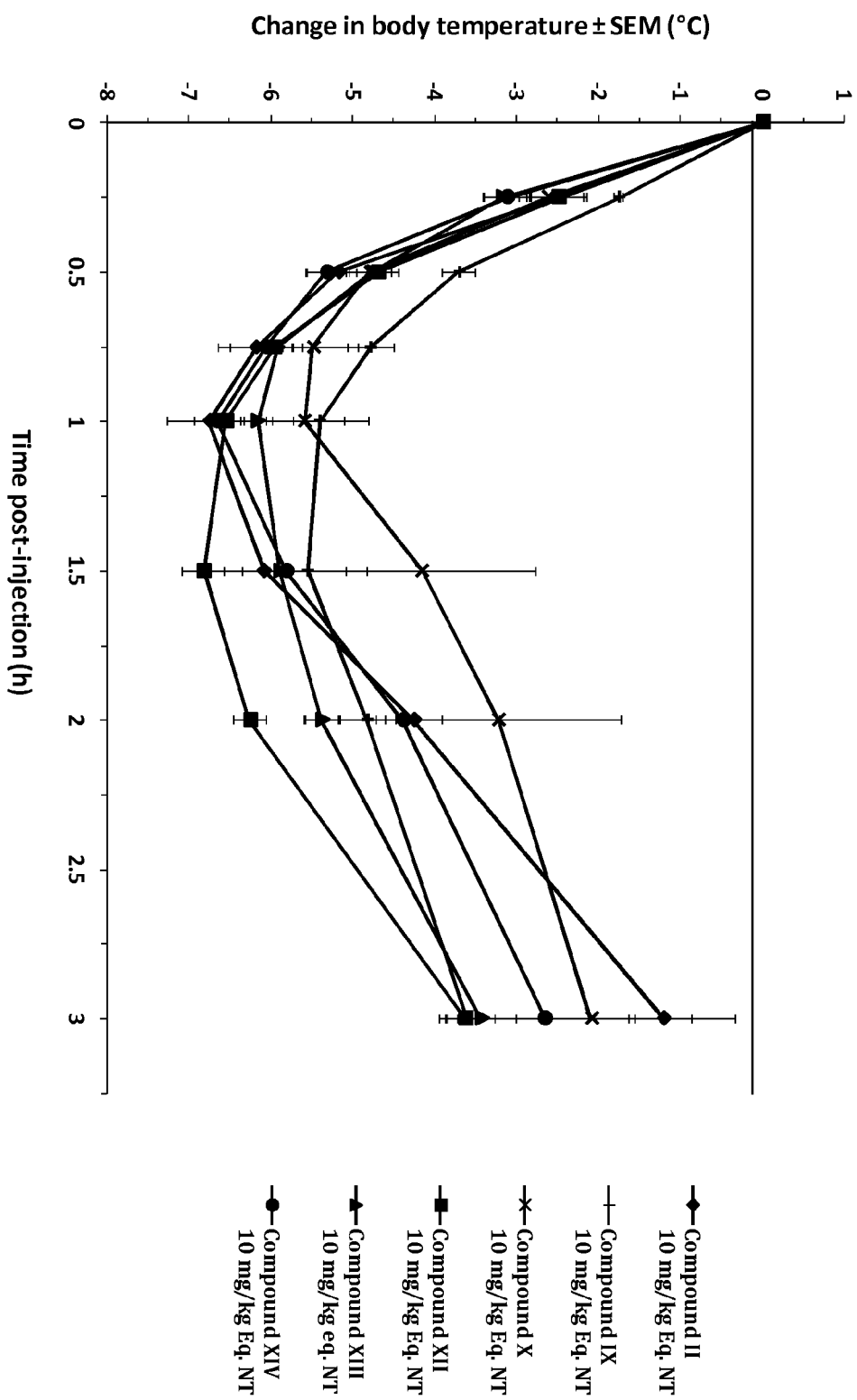

FIG. 9. Comparison of the hypothermic response in Swiss (CD-1) mice of neurotensin conjugates comprising distinct linkers between the N-terminal SEQ ID NO: 9 activator group and the C-terminal NT(6-13) or NT(8-13) moiety. Conjugates comprising either no linker group (compound IX), a GGG (compound X), Ahx (compound XII), PEG2 (compound XIII) or PEG6 (compound XIV) linker were injected i.v. (bolus) in mice at the same dose level of 10 mg/kg eq. NT.

Figure 10:
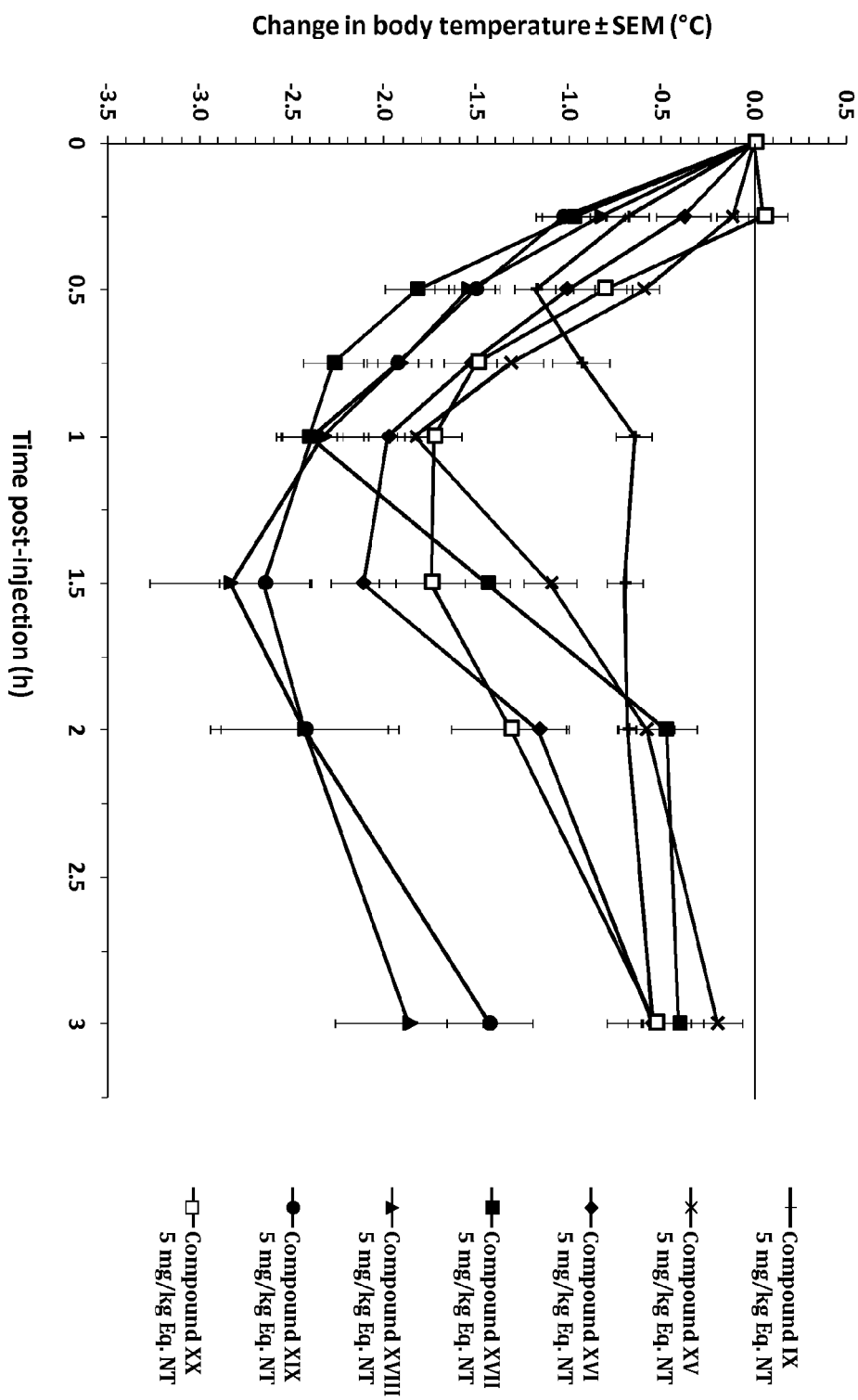

FIG. 10. Comparison of the hypothermic response in Sprague-Dawley rats of tandem SEQ ID NO: 9-NT(8-13) or SEQ ID NO: 11-NT(8-13) conjugates comprising NT(8-13) analogs. Conjugates comprising either [Tle12] (compound XV), [Lys8, Tle12] (compound XVI and compound XX), [Lys9, Tle12] (compound XVII), [Trp11, Tle12] (compound XVIII) or [Lys8, Trp11, Tle12] (compound XIX) substitutions in the NT(8-13) sequence were injected i.v. (bolus) in rats at the same dose level of 5 mg/kg eq. NT.

Figure 11:
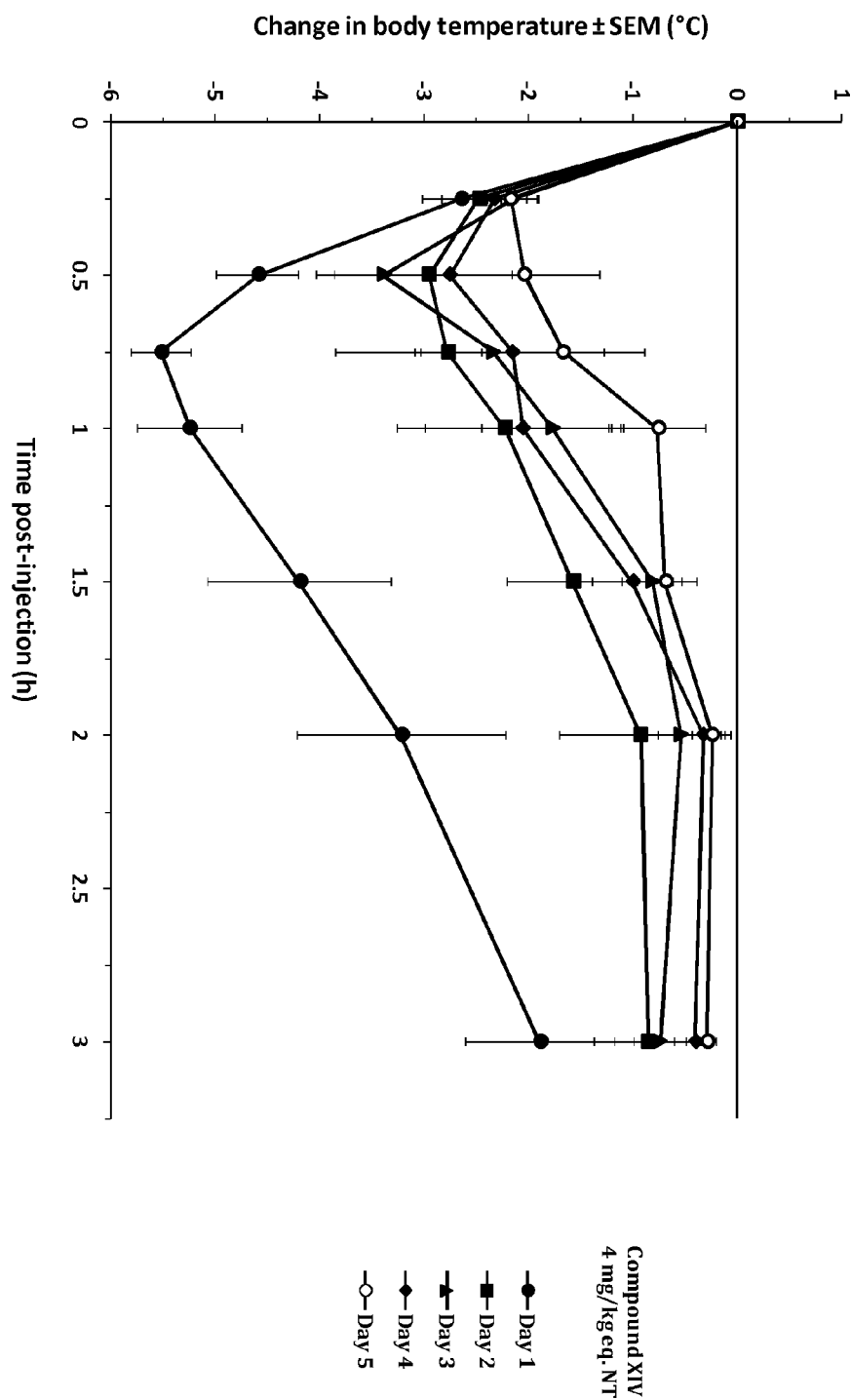

FIG. 11. Effect of repeated administration of compound XIV on body temperature. Swiss (CD-1) mice were given daily i.v. (bolus) injections of compound XIV at the dose of 4 mg/kg eq. NT during 4 days and the hypothermic response was assessed each day during 3 hours following treatment administration. Compound XIV retained a significant and stable hypothermic effect over days.

Figure 12:
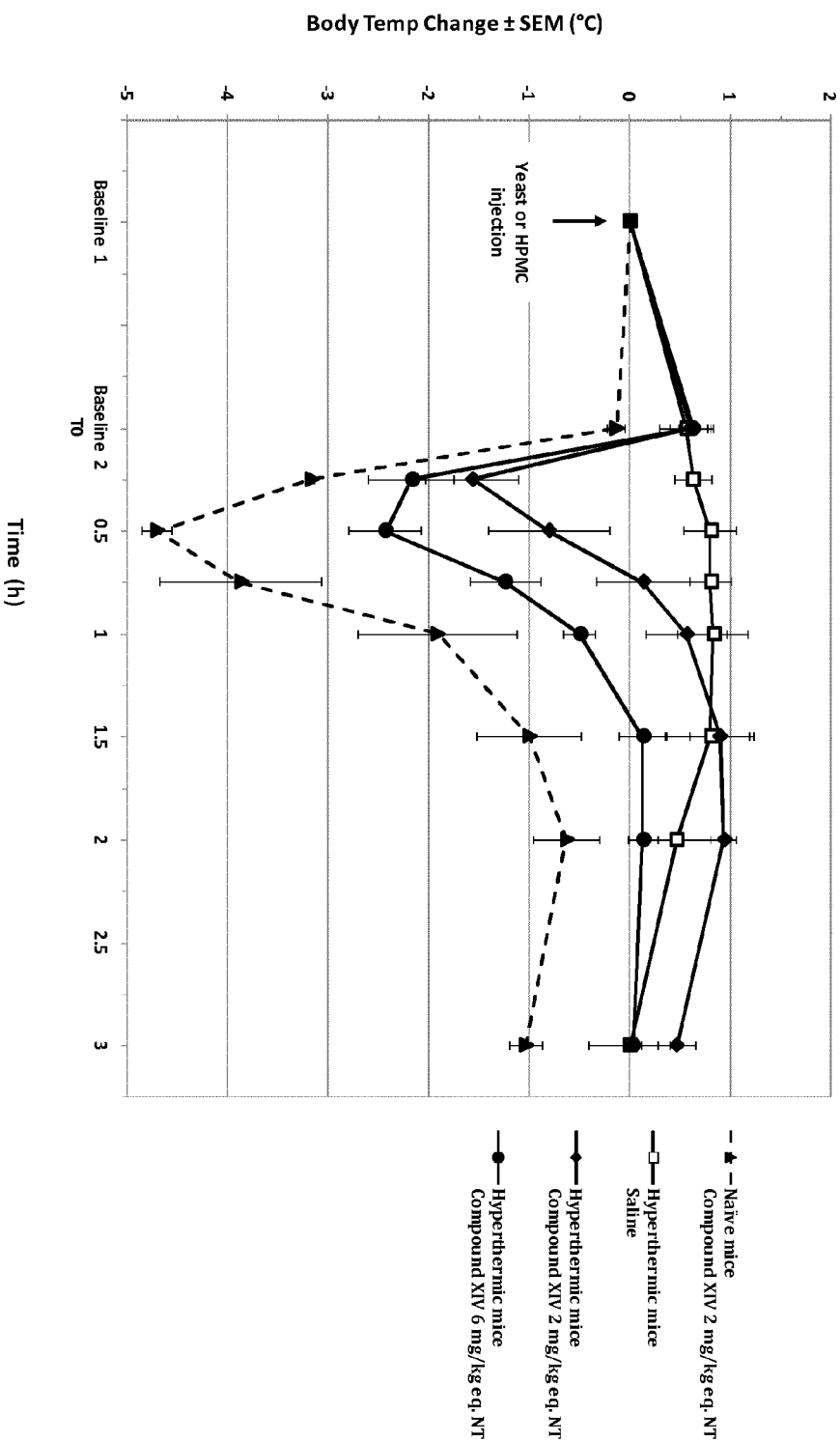

FIG. 12. Antipyretic effect of compound XIV in a mouse model of yeast-induced hyperthermia. Subcutaneous injection of a yeast suspension in NMRI mice caused a +0.8° C. rise in rectal temperature (Baseline 2, hyperthermic vs. naïve mice). Compound XIV injected i.v. (bolus) at the indicated dose levels not only showed an antipyretic effect but also induced a strong and dose-dependent hypothermia at intermediate and high dose levels.

Figure 13:
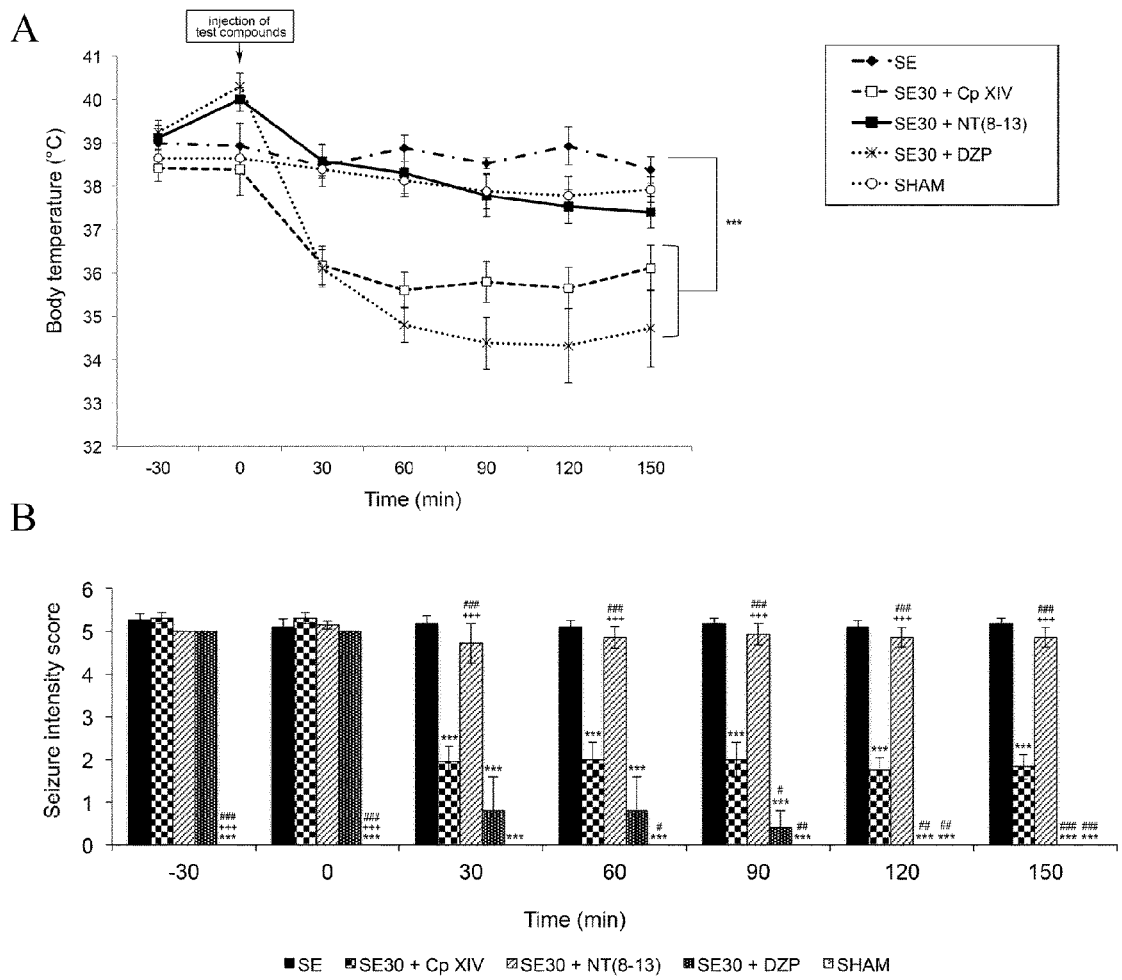

FIG. 13: Effects of compound XIV on body temperature and seizure intensity in status epilepticus (SE). Mice were administered the pro-convulsant drug kainite (KA) which induced stage 5 or stage 6 seizures after 2 hours characteristic of SE, and often associated with hyperthermia. Compound XIV administered 30 minutes after SE onset (SE30) at the dose of 2 or 4 mg/kg eq. NT invariably led to transient hypothermia which persisted at least 2 hrs (FIG. 13A). Hypothermia induced by compound XIV was associated with a significant decrease of seizures in the SE30+ compound XIV group. A subset of animals was administered i.p. a high dose of diazepam (DZP) used as a positive control for its anticonvulsant effects in seizure models. No significant variations of body temperature or seizure intensity were observed when neurotensine (NT8-13) was administered 30 min after SE onset, as compared with SE animals (FIG. 13B).

Figure 14:
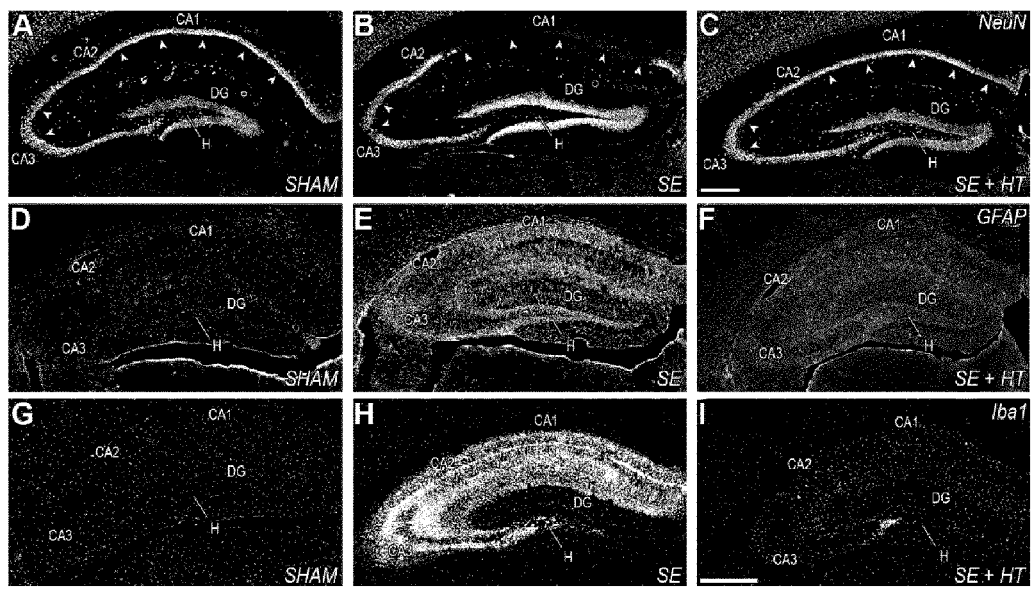
Figure 14:
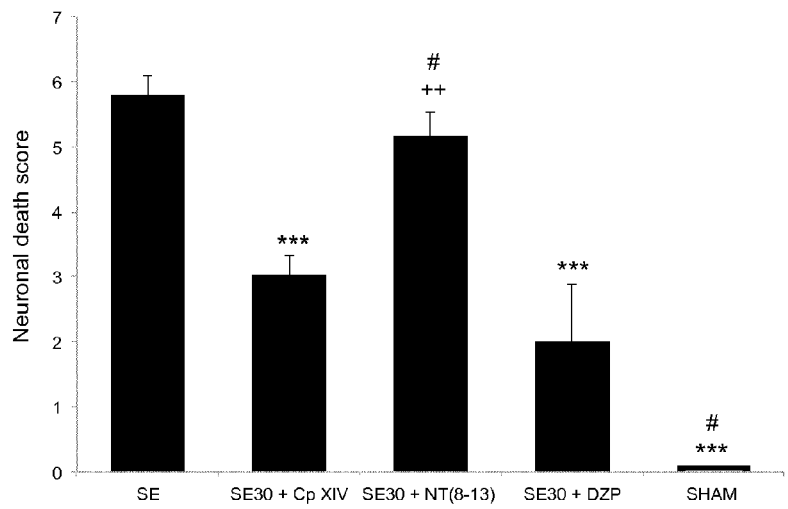

FIG. 14. Neuroprotective and anti-neuroinflammatory effects of compound XIV in mice with severe excitotoxic damage and neuroinflammation following SE induced by KA. Immunohistochemical labeling (FIG. 14A) was used to assess the extent of brain damage in coronal sections of the hippocampal formation from SHAM (A, D, G), SE (B, E, H) and SE+ compound XIV (SE+HT) (C, F, I) animals. Neurons were labeled in A, B and C with the anti-NeuN antibody that labels a neuron-specific nuclear protein. Arrowheads point to neurons in the CA1 and CA3 pyramidal cell layers as well as in the hilar region (H) of the dentate gyrus (DG). Neuroinflammation was assessed with anti-GFAP (D, E, F) and Iba1 (G, H, I) antibodies to monitor astrocytic and microglial reactivity, respectively. Small arrows point to reactive astrocytes and microglia. Scale bar=500 μm. SE-induced gliosis involved microglia and astroglial cell types. In SHAM animals, a basal labeling for GFAP and Iba1 was detected in the hippocampus (FIG. 14A). In SE animals, a very strong activation of glial cells occurred in all hippocampal layers. This inflammatory response was significantly decreased when compound XIV (SE+HT) was administered 30 min after SE onset. NeuN and Fluoro-jade C labeling were used to quantify neuronal death and the effects of compound XIV (FIG. 14B). In SHAM animals, no neuronal death was observed in the hippocampus. In SE animals, major neuronal death was observed in CA1-3 pyramidal cell layers and DG. Neurodegeneration observed in SE animals was significantly decreased when compound XIV or DZP was administered 30 min after SE onset, but no changes were observed when NT(8-13) was administered (FIG. 14 B).

Figure 15:
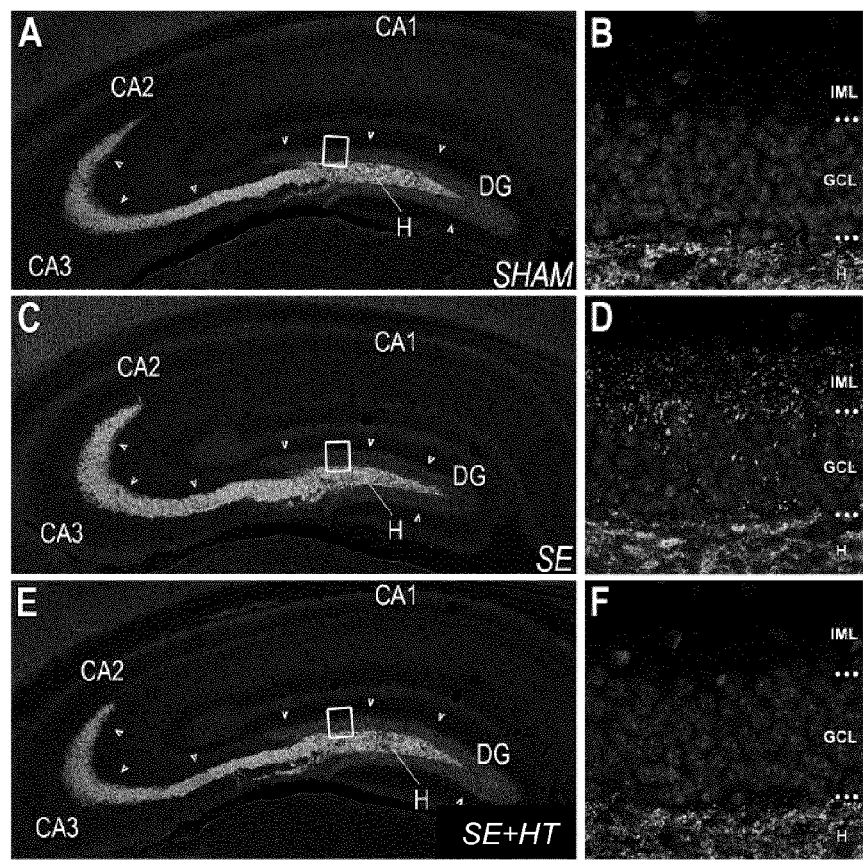
Figure 15:
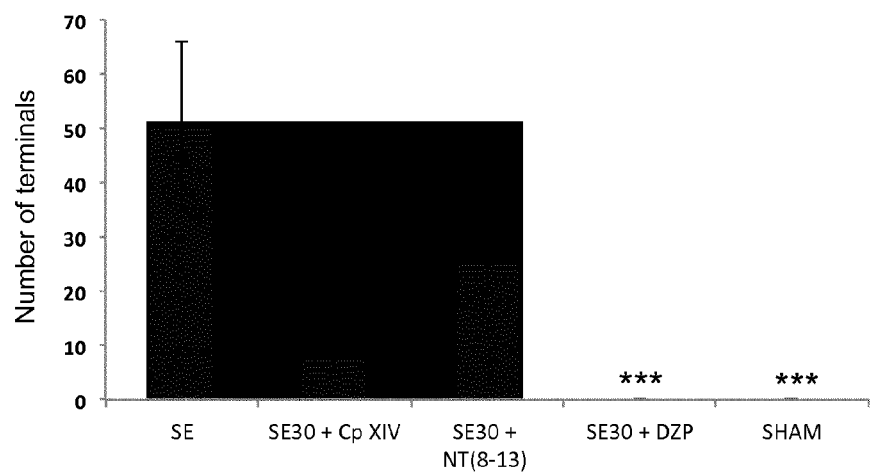

FIG. 15: Compound XIV attenuates mossy fiber sprouting in the hippocampus 8 weeks after SE. Aberrant sprouting of mossy fibers, the axons of dentate granule cells, occurs in the inner molecular layer (IML) in response to hilar cell loss and is well-established in animal seizure models and in epilepsy in humans. The effects of compound XIV on sprouting were assessed 8 weeks after induction of SE with immunohistochemical labeling for the zinc vesicular transporter 3 (ZnT3). In SHAM animals, mossy fiber terminals were present in the hilus and stratum lucidum of the CA3 region and no terminals were observed in the IML of the DG. In SE animals, mossy fiber terminals were observed within the IML. In comparison with SE animals, the number of terminals innervating the IML was considerably reduced in animals administered with compound XIV (SE+HT, FIG. 15A) or DZP 30 min after SE onset but relatively unchanged when NT(8-13) was administered (FIGS. 15A, 15B).

Figure 16:
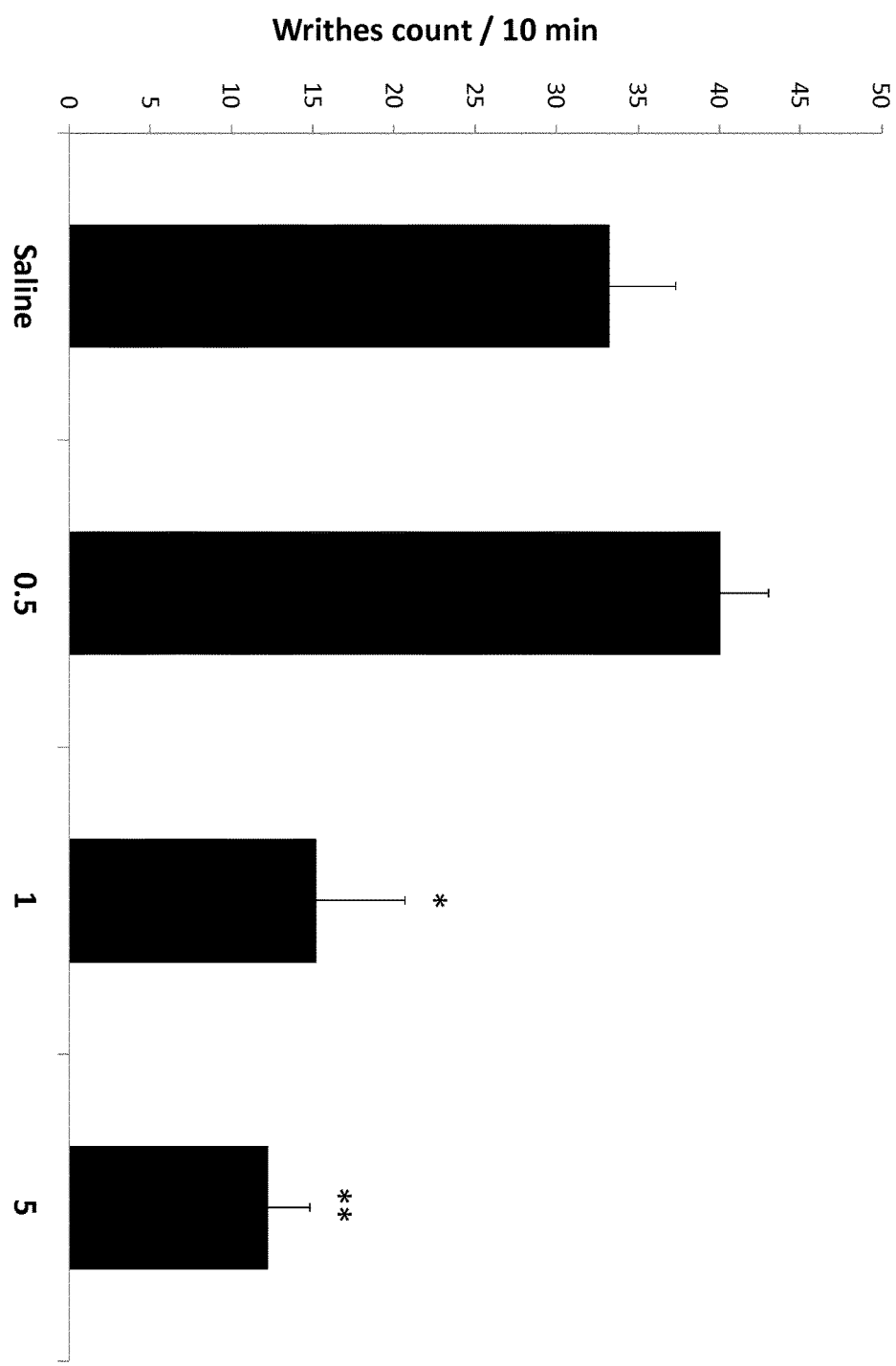

FIG. 16. Antinociceptive effect of compound XIV in the writhing test in mice. Compound XIV was injected i.v. (bolus) at the increasing dose levels of 0.5, 1 and 5 mg/kg eq. NT in mice 30 min before intraperitoneal injection of 10 mL/kg acetic acid 0.5%. The number of abdominal stretches occurring in each mouse during a 10 min period starting 5 min following i.p. injection of acetic acid was measured (writhe count/10 min).

DETAILED DESCRIPTION OF THE INVENTION

The present invention provides novel neurotensin-based compounds, pharmaceutical compositions comprising the same, and the uses thereof, e.g., to induce a controlled reduction of body temperature (e.g., hypothermia or normothermia), a controlled anti-convulsant effect, or analgesia in subjects in need thereof.

More particularly, an object of the invention resides in a compound comprising a neurotensin polypeptide covalently coupled to an activator group comprising the amino acid sequence M-aa1-R-L-R, wherein aa1 is a Proline residue or an analog thereof.

As illustrated in the Examples section, the activated neurotensin compounds of the invention exhibit highly improved biological properties, including both enhanced BBB permeability and high resistance to proteolytic cleavage when compared to native NT. The compounds exhibit potent biological activity at low dose levels upon systemic administration, with very rapid onset of action together with high tolerance and safety profiles. In particular, the compounds of the invention i) induce a central hypothermic effect up to 80-fold greater than that obtained with native NT, ii) do not induce hypothermia-associated shivering, iii) demonstrate a plateau effect that prevents potentially lethal exaggerated hypothermia, iv) show a significant safety margin between the minimal effective dose (MED) upon intravenous (bolus) injection and the maximal tolerated dose (MTD), v) retain significant biological activity upon repeated intravenous administration, demonstrating their suitability for conditions requiring repeated or subchronic treatment, vi) exhibit potent antipyretic activities, vii) effectively reduce or halt motor seizures, viii) exhibit neuroprotective and anti-neuroinflammatory activities, ix) effectively reduce aberrant axonal sprouting following seizures and in epilepsy, and x) induce significant analgesic effects, demonstrating unexpected beneficial effects and efficacy in distinct pathophysiological conditions.

The compounds of the invention essentially comprise a neurotensin polypeptide covalently coupled to an activator group. The activator group may be covalently attached to the neurotensin polypeptide, either directly or indirectly, via a linker group. The compounds may also be represented by the following formula (I):

NT-Linker-AG    (I)

wherein NT designates any polypeptide having neurotensin activity; Linker is a crosslinking molecule or platform having at least two reactive groups, different or not; and AG is an activator group comprising the above-specified amino acid sequence. It should be understood that the spatial arrangement, the linking strategy and the anchoring points of the moieties to each other may be adjusted in order to provide optimized activity.

Neurotensin Polypeptide

The term neurotensin polypeptide designates any polypeptide having neurotensin activity, such as neurotensin, a neurotensin analog, or a polypeptide agonist of a neurotensin receptor. The term "analog" as mentioned above includes any variants or fragments of a wild-type neurotensin retaining one or several biological activities of neurotensin, such as the ability to induce hypothermia or analgesia. More preferably, a neurotensin polypeptide designates native neurotensin or an analog thereof. In a further preferred embodiment, the term neurotensin polypeptide includes human neurotensin or fragments or variants thereof retaining one or several biological activities of neurotensin.

Human wild-type neurotensin is a 13 amino acid peptide having the following sequence: pELYENKPRRPYIL-OH (SEQ ID NO: 1).

A neurotensin polypeptide of the invention therefore includes, preferably, any polypeptide comprising:

(i) SEQ ID NO: 1, (ii) a natural variant of (i), (iii) a fragment of (i) or (ii), or (iv) an analog of any sequence of (i)-(iii), preferably comprising one or more amino acid substitutions or modifications, even more preferably comprising a substitution or modification of 1, 2, 3, 4, 5, 6, or 7 amino acid residues, even more preferably of 1, 2, 3 or 4 amino acid residues, said polypeptide having the ability to elicit one or several biological activities of neurotensin, such as hypothermia or analgesia.

A fragment of a sequence as used herein designates any fragment comprising at least 4 consecutive amino acids of said sequence, more preferably at least 5. In this regard, preferred neurotensin polypeptides according to the invention comprise neurotensin fragments comprising at least amino acids 8-13 of human neurotensin ("NT(8-13)"), or amino acids 6-13 of human neurotensin ("NT(6-13)"), or amino acids 2-13 of human neurotensin ("NT(2-13)"). Such fragments comprising at least the C-terminal NT(8-13)

fragment have been reported to elicit most, if not all, of the biological activities of neurotensin. Corresponding amino acid sequences are provided below:

```
NT(8-13):    RRPYIL         (SEQ ID NO: 2)
NT(6-13):    KPRRPYIL       (SEQ ID NO: 3)
NT(2-13):    LYENKPRRPYIL.  (SEQ ID NO: 4)
```

In a particular embodiment, the sequence of the neurotensin polypeptide according to the invention comprises 1, 2, 3, or 4 amino acid modifications (e.g., substitution, insertion, or chemical modification) as compared to the sequence of a wild-type neurotensin polypeptide or fragment thereof. In this regard, the following amino acid substitutions and modifications can be made to NT or fragments thereof, individually or in combination(s), to produce biologically active analogs of neurotensin for use in the invention:

- N-terminus acetylation, to generate, e.g., acetyl-NT (2-13), acetyl-NT(6-13), or acetyl-NT(8-13);
- Substitution of Arg8 by (D)-Arg, Lys, (D)-Lys, HLys (homolysine), Dab (diaminobutyric acid), Orn (ornithin), (D)-Orn or alpha-desamino-N,N-dimethylhomolysine, to generate, e.g., [(D)-Lys8]NT(8-13), [Lys8]NT(8-13) or [HLys8]NT(8-13);
- Substitution of Arg9 by Lys, (D)-Lys, Orn, (D)-Orn, Dab, (D)-Arg, HLys (homolysine), or alpha-desamino-N,N-dimethylhomolysine to generate, e.g., [Lys9]NT, [Lys9]NT(8-13), [(D)-Orn9]NT or [(D)-Orn9]NT(8-13);
- Substitution of Tyr11 by Trp, (D)-Trp, neoTrp, (D)-Tyr, Phe, (D)-Phe, Nal (naphtylalanine) or (D)-3,1-naphtylalanine to generate, e.g., [Trp11]NT(8-13), [(D)-Tyr11]NT(8-13), [Trp11]NT or [(D)-Tyr11]NT;
- Substitution of Ile12 by Tle (terbutyl-leucine) to generate, e.g., [Tle12]NT(8-13) or [Tle12]NT;
- Combined substitutions of Arg8, Arg9, Tyr11 and Ile12, to generate, e.g., [(D)-Lys8, Trp11, Tle12]NT(8-13), [Lys9, Trp11, Tle12]NT(8-13), [Lys8, Tle12]NT(8-13), [Lys9, Tle12]NT(8-13), [Trp11, Tle12]NT(8-13), [Lys8, Trp11, Tle12]NT(8-13) or [HLys8, Tle12]NT(8-13);
- Modification of peptide bonds at positions 8-9, 9-10, 10-11, 11-12 or 12-13 with CH$_2$NH (psi) reduced bonds; and/or
- Cyclization of a dimer of NT(8-13), with or without any of the above possible amino acid substitutions or modifications.

In a preferred embodiment, the neurotensin polypeptide is selected from human NT, NT(2-13), NT(6-13) or NT(8-13), or analogs thereof having from 1 to 4 amino acid modifications.

In this regard, in a most preferred embodiment, the neurotensin polypeptide is selected from [Lys8]NT(8-13), [Lys9]NT(8-13), [HLys8]NT(8-13), [(D)-Lys8]NT(8-13), [(D)-Orn9]NT(8-13), [Lys8, Lys9]NT(8-13), [(D)-Lys8, Lys9]NT(8-13), [Trp11]NT(8-13), [neoTrp11]NT(8-13), [Tle12]NT(8-13), [Trp11, Tle12]NT(8-13), [neoTrp11, Tle12]NT(8-13), [Lys8, Tle12]NT(8-13), [(D)-Lys8, Tle12]NT(8-13), [(D)-Lys8, Trp11]NT(8-13), [(D)-Lys8, neoTrp11]NT(8-13), [Lys8, Trp11, Tle12]NT(8-13), [(D)-Lys8, neoTrp11, Tle12]NT(8-13), [(D)-Lys8, Lys9, Trp11, Tle12]NT(8-13), [(D)-Lys8, Lys9, neoTrp11, Tle12]NT(8-13), [Lys9, Tle12]NT(8-13), [Lys9, Trp11]NT(8-13), [Lys9, neoTrp11]NT(8-13), [Lys9, Trp11, Tle12]NT(8-13), [Lys9, neoTrp11, Tle12]NT(8-13), [HLys8, Tle12]NT(8-13), [HLys8, Trp11]NT(8-13), [HLys8, neoTrp11]NT(8-13), [HLys8, Trp11, Tle12]NT(8-13), [HLys8, neoTrp11, Tle12]NT(8-13), [(D)-Orn9, Tle12]NT(8-13), [(D)-Orn9, Trp11]NT(8-13), [(D)-Orn9, neoTrp11]NT(8-13), [(D)-Orn9, Trp11, Tle12]NT(8-13), or [(D)-Orn9, neoTrp11, Tle12]NT(8-13).

In another preferred embodiment, the neurotensin polypeptide of the invention is a full-size NT, or an NT(2-13), or an NT(6-13) polypeptide comprising any of the above amino acid substitutions.

In a most preferred embodiment, the neurotensin polypeptide is NT(8-13) or an analog thereof retaining one or several biological activities of neurotensin.

Further neurotensin polypeptides or neurotensin substitutions suitable for use in the present invention are described for instance in Rivier et al., J Med Chem 1977; Tokumura et al., Chem Pharm Bull (Tokyo) 1990; Labbé-Jullié et al., J Pharm Exp Ther 1994; Tyler et al., Brain Res 1998; Podstawka-Proniewicz et al. J Phys Chem 2011; Kitabgi et al., (Mol Pharm 18, 11-19 (1980); and Patent Applications U.S. 2009/0062212, WO 2008/137720, WO 1999/52539, WO 2007/070672, WO 2010/063122 and WO 2012/000118.

Activator Group

The activated neurotensin compounds of the invention comprise an activator group, which potentiates their activity. In a general aspect, the activator group comprises any peptide sequence which binds an LDL receptor (LDLR) on the BBB. By allowing LDLR-mediated transcytosis of NT, the inventors have generated activated compounds with surprising biological activity. In this respect, in a more preferred embodiment, the activator group comprises the amino acid sequence M-aa1-R-L-R, wherein aa1 is a proline residue ("P") or an analog thereof. In the above formula, M designates methionine, R designates arginine, and L designates leucine. As shown in the Examples section, such an activator group confers on the activated neurotensin molecules of the invention improved biological activity and pharmacologically active form. In particular, the grafting of such an activating group generates activated neurotensin molecules, which are up to 80 times more potent in reducing the body temperature than endogenous NT when administered intravenously. In addition to this remarkable hypothermic effect, the compounds show an unexpected antipyretic activity. They also exhibit the potential to reduce or halt motor seizures and demonstrate a potent and unexpected neuroprotective activity by inhibiting excitotoxicity-associated neuronal death and neuroinflammation, and by reducing aberrant axonal sprouting associated with convulsions and epilepsy. In addition, the activated neurotensin molecules of the invention display very good pharmacokinetic and pharmacodynamic profiles, with a rapid onset of action upon systemic administration, a strong hypothermic activity at low dose levels, a very good safety profile with no hypothermia-associated shivering, a plateau effect that prevents potentially lethal exaggerated hypothermia and a 400-fold safety margin between the MED and the MTD. Finally, the compound showed a significant analgesic effect by intravenous administration.

The invention therefore relates to an activated neurotensin compound, wherein said compound comprises an activator group comprising the amino acid sequence M-aa1-R-L-R, aa1 being a Proline residue ("P") or an analog thereof. Preferably the proline analog is selected from Pip and Thz. Pip stands for pipecolic acid, and Thz stands for thiazolidine-4-carboxylic acid.

According to preferred embodiments, the activator group comprises one of the following amino acid sequences:

```
M-P-R-L-R;           (SEQ ID NO: 5)

M-Pip-R-L-R;         (SEQ ID NO: 6)
or

M-Thz-R-L-R.         (SEQ ID NO: 7)
```

In a further particular embodiment, the amino acid sequence in the activator group comprises a further N-terminal Cysteine residue ("C") in configuration L or D, i.e., comprises the amino acid sequence C-M-aa1-R-L-R or c-M-aa1-R-L-R, wherein aa1 is as defined above. In a most preferred embodiment the N-terminal Cysteine residue "C" is in configuration D.

In another particular embodiment, the amino acid sequence in the activator group comprises two further C-terminal residues, i.e., comprises the sequence M-aa1-R-L-R-aa2-aa3, preferably c-M-aa1-R-L-R-aa2-aa3, wherein aa1 is as defined above, aa2 is Gly or its analog Sar (sarcosine), and aa3 is Cys or its analog Pen (penicillamine).

Specific and most preferred activator groups comprise one of the following amino acid sequences:

```
c-M-P-R-L-R-G-C          (SEQ ID NO: 8)

c-M-Pip-R-L-R-Sar-C      (SEQ ID NO: 9)

c-M-Thz-R-L-R-G-Pen      (SEQ ID NO: 10)

c-M-Pip-R-L-R-Sar-Pen.   (SEQ ID NO: 11)
```

Design of Activated Neurotensin

Preferred activated neurotensin molecules of the invention comprise one neurotensin polypeptide and one activator group. However, in alternative embodiments, it may be advantageous to combine several NT molecules with one activator group, or conversely. In this regard, particular compounds of the invention have the formula $(NT)_1$-Linker-AG or NT-Linker-$(AG)_1$, wherein 1 is an integer comprised between 2 and 5, and typically 1 is 2 or 3.

The activator group is preferably covalently linked to the neurotensin molecule. Coupling can be performed by any reaction or process that is generally known per se in the art, such as chemical, biochemical or enzymatic reaction, or by genetic engineering when the neurotensin polypeptide and activator groups comprise only natural amino acids.

Coupling can be carried out at any site of the activator group and neurotensin polypeptide where reactive functions such as —OH, —SH, —$CO_2H$, —$NH_2$, —$SO_3H$, —CN, —N3, —NCS, -maleimide or succinimide ester or —$PO_2H$ are naturally present or have been introduced. Thus, coupling can be made at the N-terminus, or at the C-terminus, and/or at a reactive group carried by a side chain. The activator group can be coupled directly to the neurotensin polypeptide by a covalent bond. Alternatively, the activator group can also be coupled indirectly by means of a linker group. Covalent chemical coupling preferably includes the use of bi- or multifunctional agents containing alkyl, aryl or peptide groups by esters, aldehydes or alkyl or aryl acids, ketones, anhydride, sulfhydryl or hydroxyl groups, groups derived from cyanogen bromide or chloride, azides, nitriles, maleimides, carbonyldiimidazole, succinimide esters or sulfonic halides. A preferred chemical coupling agent is sulfo-EMCS (N-epsilon-Maleimidocaproyl-oxysulfosuccinimide ester), which may be added to, e.g., the neurotensin polypeptide and subsequently used to covalently link the activator group.

Examples of suitable linkers include mono-, di-, tri-, or multi-amino acids, comprising for example Lys, Glu, Asp, polyLys, a dipeptide such as Gly-Lys or a multi aminoacid such as GGG or $G_45$. Other linkers include, e.g., succinic acid, Ahx (aminohexanoic acid) or a PEG (polyethylene glycol) molecule.

In a preferred embodiment, the neurotensin polypeptide and activator group are coupled using a linker selected from PEG molecules. Any PEG molecule may be used, particularly PEG2 (12-amino-4,7,10-trioxadodecanoic acid), PEG3, PEG4, PEGS, or PEG6 (21-amino-4,7,10,13,16,19-hexaoxaheneicosanoic acid). More preferably, the linker comprises a PEG2 or PEG6 molecule, even more preferably PEG6.

In another preferred embodiment, the neurotensin polypeptide and activator group are coupled directly by means of a peptide bond.

In another preferred embodiment, the neurotensin polypeptide and activator group are coupled using a flexible linker selected from a polyG molecule, more preferably a G amino acid or a GGG tripeptide, or the linear aminohexanoic acid.

In another preferred embodiment, the neurotensin polypeptide and activator group are coupled using a cleavable disulfide bond.

In another preferred embodiment, the neurotensin polypeptide and activator group are coupled using a heterobifunctional crosslinker, more preferably the sulfo-EMCS reagent.

A list of most preferred activated neurotensin molecules of the invention is provided in the following Table A.

TABLE A
| Compound | Formula | Chemical structure | MW (g/mol) | Net charge (pH 7.4) |
|---|---|---|---|---|
|  | NT | pELYENKPRRPYIL-OH | 1672.92 | +1 (3+/2−) |
| I | NT-SEQ ID NO: 8 | pELYENKPRRPYIL-OH 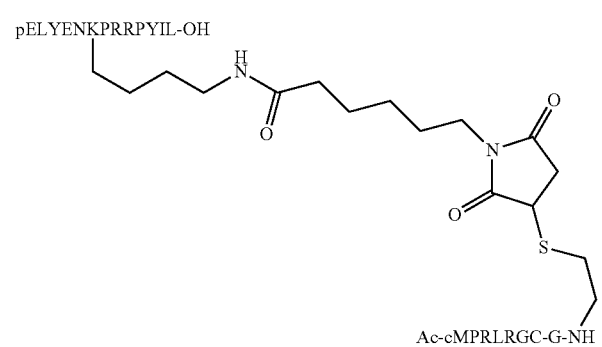 Ac-cMPRLRGC-G-NH | 2957.60 | +2 (4+/2−) |
| II | NT-SEQ ID NO: 9 | pELYENKPRRPYIL-OH 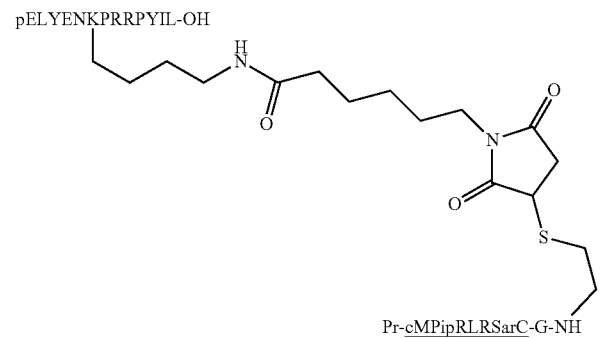 Pr-cMPipRLRSarC-G-NH | 2999.60 | +2 (4+/2−) |
| III | NT-SEQ ID NO: 10 | pELYENKPRRPYIL-OH 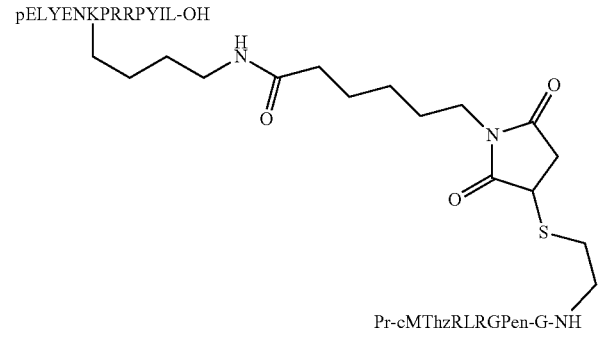 Pr-cMThzRLRGPen-G-NH | 3017.64 | +2 (4+/2−) |
| IV | NT-SEQ ID NO: 11 | pELYENKPRRPYIL-OH 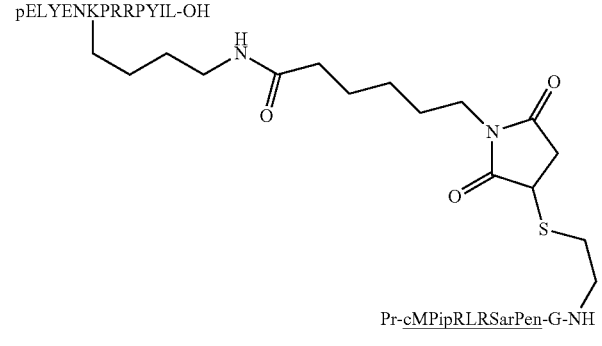 Pr-cMPipRLRSarPen-G-NH | 3027.65 | +2 (4+/2−) |

TABLE A-continued

| Compound | Formula | Chemical structure | MW (g/mol) | Net charge (pH 7.4) |
|---|---|---|---|---|
| V | NT(2-13)-SEQ ID NO: 9 | Ac-LYENKPRRPYIL-OH with side chain linker to Pr-cMPipRLRSarC-G-NH | 2930.54 | +2 (4+/2−) |
| VI | NT(6-13)-SEQ ID NO: 9 | Ac-KPRRPYIL-OH with side chain linker to Pr-cMPipRLRSarC-G-NH | 2410.99 | +3 (4+/1−) |
| VII | Lys-NT(8-13)-SEQ ID NO: 9 | Ac-KPRRPYIL-OH with side chain linker to Pr-cMPipRLRSarC-G-NH | 2313.88 | +3 (4+/1−) |
| VIII | NT(8-13)-SS-SEQ ID NO: 9 | $H_2N$-...RRPYIL-OH with disulfide to Pr-cMPipRLRSarC-NH | 2051.6 | +4 (5+/1−) |
| IX | SEQ ID NO: 9-NT(8-13) | Pr-cMPipRLRSarC-RRPYIL-OH | 1816.27 | +3 (4+/1−) |
| X | SEQ ID NO: 9-GGG-NT(6-13) | Pr-cMPipRLRSarC-GGG-KPRRPYIL-OH | 2212.71 | +4 (5+/1−) |
| XI | SEQ ID NO: 9-Ahx-NT(6-13) | Pr-cMPipRLRSarC-Ahx-KPRRPYIL-OH | 2154.71 | +4 (5+/1−) |
| XII | SEQ ID NO: 9-Ahx-NT(8-13) | Pr-cMPipRLRSarC-Ahx-RRPYIL-OH | 1929.4 | +3 (4+/1−) |
| XIII | SEQ ID NO: 9-PEG2-NT(8-13) | Pr-cMPipRLRSarC-PEG$_2$-RRPYIL-OH | 1963.4 | +3 (4+/1−) |
| XIV | SEQ ID NO: 9-PEG6-NT(8-13) | Pr-cMPipRLRSarC-PEG$_6$-RRPYIL-OH | 2151.7 | +3 (4+/1−) |
| XV | SEQ ID NO: 9-[Tle12]NT(8-13) | Pr-cMPipRLRSarC-RRPYTleL-OH | 1816.29 | +3 (4+/1−) |

TABLE A-continued

| Compound | Formula | Chemical structure | MW (g/mol) | Net charge (pH 7.4) |
|---|---|---|---|---|
| XVI | SEQ ID NO: 9-[Lys8, Tle12]NT(8-13) | Pr-cMPipRLRSarC-KRPYTIeL-OH | 1788.27 | +3 (4+/1−) |
| XVII | SEQ ID NO: 9-[Lys9, Tle12]NT(8-13) | Pr-cMPipRLRSarC-RKPYTIeL-OH | 1788.27 | +3 (4+/1−) |
| XVIII | SEQ ID NO: 9-Tle12]NT(8-13) | Pr-cMPipRLRSarC-RRPWTIeL-OH | 1839.32 | +3 (4+/1−) |
| XIX | SEQ ID NO: 9-[Lys8, Trp11, Tle12]NT(8-13) | Pr-cMPipRLRSarC-KRPWTIeL-OH | 1811.31 | +3 (4+/1−) |
| XX | SEQ ID NO: 11-[Lys8, Tle12]NT(8-13) | Pr-cMPipRLRSarPen-KRPYTIeL-OH | 1816.33 | +3 (4+/1−) |

Detailed methods of producing activated neurotensin molecules of the invention are disclosed in the Examples section. In this respect, the invention also relates to a method for preparing an activated neurotensin molecule, comprising a step of covalent (direct or indirect) coupling between a neurotensin polypeptide and an activator group as defined above. The method may comprise a further step of collecting or purifying the activated neurotensin, and/or a further optional step of modifying the activated neurotensin, and/or a further optional step of formulating the activated neurotensin with an acceptable excipient.

In a particular embodiment, the neurotensin polypeptide and activator group are first synthesized separately and then covalently linked by, e.g., chemical, enzymatic or biochemical coupling. As disclosed above, coupling can be made through various reactive functions present and/or inserted in the neurotensin and/or activator group, and optionally using a suitable linker.

In another particular embodiment, the neurotensin polypeptide and activator group are synthesized directly as a single molecule. For instance, the activated neurotensin molecule may be produced on a polypeptide synthesizer as a unique molecular entity. Alternatively, the activated neurotensin molecule may be produced by genetic fusion and expression in a recombinant host cell. Such a method is feasible when both components comprise natural amino acids.

In this regard, the invention also relates to a nucleic acid molecule encoding an activated neurotensin of the invention, wherein the neurotensin polypeptide and activator group comprise naturally-occurring amino acids and are coupled by an amino acid bond or linker.

A further object of the invention is a cloning or expression vector (e.g., a plasmid, phage, virus, cosmid, etc.) comprising such a nucleic acid molecule, and a recombinant host cell comprising such a nucleic acid or vector.

The activated neurotensin molecules of the invention may be modified to further increase their activity or improve pharmacokinetic properties using techniques known per se in the art. For instance, they may be bound to a polymer (PEG, albumin), or modified by addition of a lipophilic substituent or by addition of a chemically reactive group. Also, naturally occurring amino acids may be replaced by peptidomimetics or amino acid analogs and/or cyclic polypeptides may be generated.

Pharmaceutical Compositions and Methods

The invention also relates to a pharmaceutical composition comprising an activated neurotensin molecule as defined above and one or more pharmaceutically acceptable excipients.

The activated neurotensin can be used in the form of any pharmaceutically acceptable salt. The expression "pharmaceutically acceptable salt" refers to, for example and in a non-restrictive way, pharmaceutically acceptable base or acid addition salts, hydrates, esters, solvates, precursors, metabolites or stereoisomers.

The expression "pharmaceutically acceptable salt" refers preferably to nontoxic salts, which can be generally prepared by reacting a free base with a suitable organic or inorganic acid. These salts preserve the biological effectiveness and the properties of free bases. Representative examples of such salts include water-soluble and water-insoluble salts such as acetates, N-methylglucamine ammonium, amsonates (4,4-diaminostilbene-2,2'-disulphonates), benzenesulphonates, benzonates, bicarbonates, bisulphates, bitartrates, borates, hydrobromides, bromides, buryrates, camsylates, carbonates, hydrochlorates, chlorides, citrates, clavulanates, dichlorhydrates, diphosphates, edetates, calcium edetates, edisylates, estolates, esylates, fumarates, gluceptates, gluconates, glutamates, glycolylarsanylates, hexafluorophosphates, hexylresorcinates, hydrabamines, hydroxynaphthoates, iodides, isothionates, lactates, lactobionates, laurates, malates, maleates, mandelates, mesylates, methylbromides, methylnitrates, methyl sulphates, mucates, napsylates, nitrates, 3-hydroxy-2-naphthoates, oleates, oxalates, palmitates, pamoates (1,1-methylene-bis-2-hydroxy-3-naphtoates, or emboates), pantothenates, phosphates, picrates, polygalacturonates, propionates, p-toluenesulphonates, salicylates, stearates, subacetates, succinates, sulphates, sulphosalicylates, suramates, tannates, tartrates, teoclates, tosylates, triethiodides, trifluoroacetates and valerianates.

The invention also relates to a pharmaceutical composition comprising a nucleic acid, vector or host cell as defined above and one or more pharmaceutically acceptable excipients.

The compositions of the invention advantageously comprise a pharmaceutically acceptable excipient that can be selected from the excipients classically used in the pharmaceutical industry, such as diluents, solid carriers, stabilizers, preservatives, surfactants, etc. The composition can be formulated in a solid, semi-solid or liquid form.

Liquid compositions are preferred. Such liquid formulations, in particular injectable, can be prepared for example by dissolution or dispersion of the activated neurotensin molecules in a pharmaceutically acceptable solvent such as water, physiological saline solution, aqueous dextrose, glycerol, ethanol, oil and analogs thereof.

For solid compositions such as tablets, pills, powders, or granules, the active substance can be combined with: a) diluents, for example lactose, dextrose, sucrose, mannitol, sorbitol, cellulose and/or glycine; b) lubricants, for example silica, talc, stearic acid, its magnesium or calcium salt and/or polyethylene glycol; c) binders, for example magnesium and aluminum silicate, starch paste, gelatin, tragacanth, methylcellulose, sodium carboxymethylcellulose and/or polyvinylpyrrolidone; d) disintegrants, for example starch, agar, alginic acid or its sodium salt, or effervescent mixtures; and/or d) absorbents, dyes, flavoring agents and sweeteners. The excipients can be, for example, mannitol, lactose, starch, magnesium stearate, sodium saccharin, talc, cellulose, glucose, sucrose, magnesium carbonate and analogs of pharmaceutical quality.

For semi-solid compositions such as suppositories, the excipient can, for example, be an emulsion or oily suspension, or polyalkylene glycol-based, such as polypropylene glycol.

Further excipients suitable for use in the invention are compounds as described in WO 2012/090070 or in U.S. 2012/0172454.

The invention also relates to a kit comprising a container containing a composition as defined above and a drug delivery device or manual. The drug delivery device is preferably a syringe.

The compositions of the invention can be administered by any suitable route such as, without limitation, parenteral, oral, rectal, topical, or intranasal routes.

Parenteral administration may be performed by injection using, for example, intraperitoneal, subcutaneous, intravenous, intraocular or intramuscular injection, optionally with extended or delayed release or controlled release. Oral administration (or per os) can be made using, e.g., preparations in the form of coated or uncoated tablets, gelatin capsules, powders, pellets, suspensions or oral solutions (one such form for oral administration can be either with immediate release or with extended, delayed release or controlled release). The rectal route may be used with, e.g., preparations in the form of suppositories. Additional routes include topical routes, in particular transdermal routes such as in the form of patches, pomades or gels; intranasal routes such as in aerosol and spray form; the perlingual route; and intraocular or intraperitoneal routes.

The pharmaceutical compositions typically comprise an effective dose of an activated neurotensin of the invention. A "therapeutically effective dose" as described herein refers to the dose that gives a therapeutic effect for a given condition and administration schedule. It is typically the average dose of an active substance to administer to appreciably achieve the expected biological effect responsible for, or contributing to, the improvement of some of the symptoms associated with a disease or a pathological state. For example, in treating a lesion or a disorder of the CNS, the dose that decreases, prevents, delays, eliminates or stops one of the causes or symptoms of the disease or disorder would be therapeutically effective. A "therapeutically effective dose" of an active substance does not necessarily cure a disease or disorder but will provide a treatment for this disease or disorder so that its appearance is delayed, impeded or prevented, or its symptoms are attenuated, or its term is modified or, for example, is less severe, or the recovery of the patient is accelerated.

It is understood that the "therapeutically effective dose" for a person in particular will depend on various factors, including the activity/effectiveness of the active substance, its time of administration, its route of administration, its rate of elimination and its metabolism, and the severity of the disease (or disorder) treated on a preventive or curative basis, as well as the age, weight, overall health, sex and/or diet of the patient. The effective dose may thus be adjusted by the skilled artisan. Generally, however, the effective dose (expressed in molar equivalents to neurotensin) is comprised between 0.001 and 10 mg/kg, more preferably between 0.002 and 5 mg/kg. In a preferred range, the effective dose is comprised between 0.01 and 2 mg/kg. Such dose ranges are particularly suitable for parenteral injection, particularly for intravenous (bolus) injection.

The molecules and compositions of the invention can be used to induce pharmacological hypothermia in mammals, and to treat any disease or condition that can benefit from hypothermia.

The invention is particularly suited to treat CNS disorders associated with global, focal and neonatal CNS ischemia, CNS trauma, heart surgeries, pain and hyperthermia. More specifically, the invention is suited to prevent, reduce or minimize the excitotoxic neuronal damage and neuroinflammation caused in the CNS of a subject by cardiac arrest, stroke, neonatal ischemia, seizures, severe traumatic head and spinal cord injuries, or heart surgeries, to reduce hyperthermia associated with ICH, sepsis or any viral, bacterial or parasitic infection associated with fever, and to reduce pain.

An object of the invention concerns the use of a compound or composition as defined above to induce hypothermia in a mammalian subject and/or for treating a subject having brain damage.

A further aspect of the invention relates to a method of inducing hypothermia in a mammalian subject, comprising the systemic administration to said subject of a compound or composition as defined above.

A further aspect of the invention relates to a method of reducing body temperature in a mammalian subject, comprising the systemic administration to said subject of a compound or composition as defined above.

A further object of the invention is a method of treating a subject having brain damage, comprising the systemic administration to said subject of a compound or composition as defined above.

A further object of the invention is a method of reducing pain in a subject, comprising the systemic administration to said subject of a compound or composition as defined above.

A further object of the invention is a method of reducing seizures in a subject, comprising the systemic administration to said subject of a compound or composition as defined above.

The invention may be used to treat (e.g., protect, prevent, or reduce) the effect of brain damage in any mammalian subject, such as a human patient. It is particularly suited for treating a subject following sudden cardiac arrest, having stroke, neonatal ischemia, or seizures, following severe traumatic head and spinal cord injuries, during heart surgery, to reduce hyperthermia associated with ICH, sepsis or any viral, bacterial or parasitic infection associated with fever, or to reduce pain.

The terms "treatment," "treating," "treat" and other similar expressions refer to achieving a pharmacological and/or physiological effect, for example reduction of body temperature, and any indirect beneficial effects on the patient condition. The effect can be prophylactic or preventive in order to completely or partially prevent the aggravation of a disease or a symptom in an ill person, or its propagation in healthy subjects, and/or can be therapeutic in order to completely or partially treat a disease and/or its related harmful effects. The term "treatment" as used in the present document covers any treatment of a disease in a mammal, and more particularly in human subjects, and comprises: (a) prevention of a disease or a condition that can arise in a person predisposed to this pathology or disorder, but who has not yet been positively diagnosed, (b) the slowing of a disease (for example, by stopping its development), or (c) relief from a disease (for example, by reducing the symptoms associated with the disease). This term "treatment" also covers any administration of an active substance in order to tend, cure, relieve, improve, decrease or inhibit a condition in an individual or patient.

The invention also relates to a method of reducing a subject's body temperature, comprising administering to a subject in need thereof a compound or composition as defined above in an amount sufficient to reduce the body temperature of the subject.

The subject may be suffering from, or may have recently suffered from, e.g., sudden cardiac arrest, stroke, neonatal ischemia, brain or spinal cord injury, seizures, or hyperthermia, may be undergoing cardiac surgery, and may be in need of neuroprotection.

Further aspects and advantages of the present invention will become apparent upon consideration of the examples below, which are only illustrative in nature and do not limit the scope of the present application.

EXAMPLES

Example 1

Synthesis of Activated NT(1-13)-AG Drugs Via NT-Lys6

In a first step, full-size neurotensin pELYENKPRRPYIL-OH (NT) was coupled to various activator groups (AGs) developed by the inventors. The objective was to select the best AG/NT combinations. To synthesize such molecules we took advantage of the amine reactivity of the lysine 6 side chain in the neurotensin sequence. Commercial sulfo-EMCS (N-epsilon-Maleimidocaproyl-oxysulfosuccinimide ester) was coupled via its succinimide ester moiety on lysine 6. After purification functionalized neurotensin (NT-EMCS) was conjugated to the different thiolated AGs.

Three steps were therefore performed to achieve the final desired conjugates: synthesis of the two functionalized moieties, NT-EMCS and the thiolated AGs, and the coupling thereof. These steps are schematically represented below:

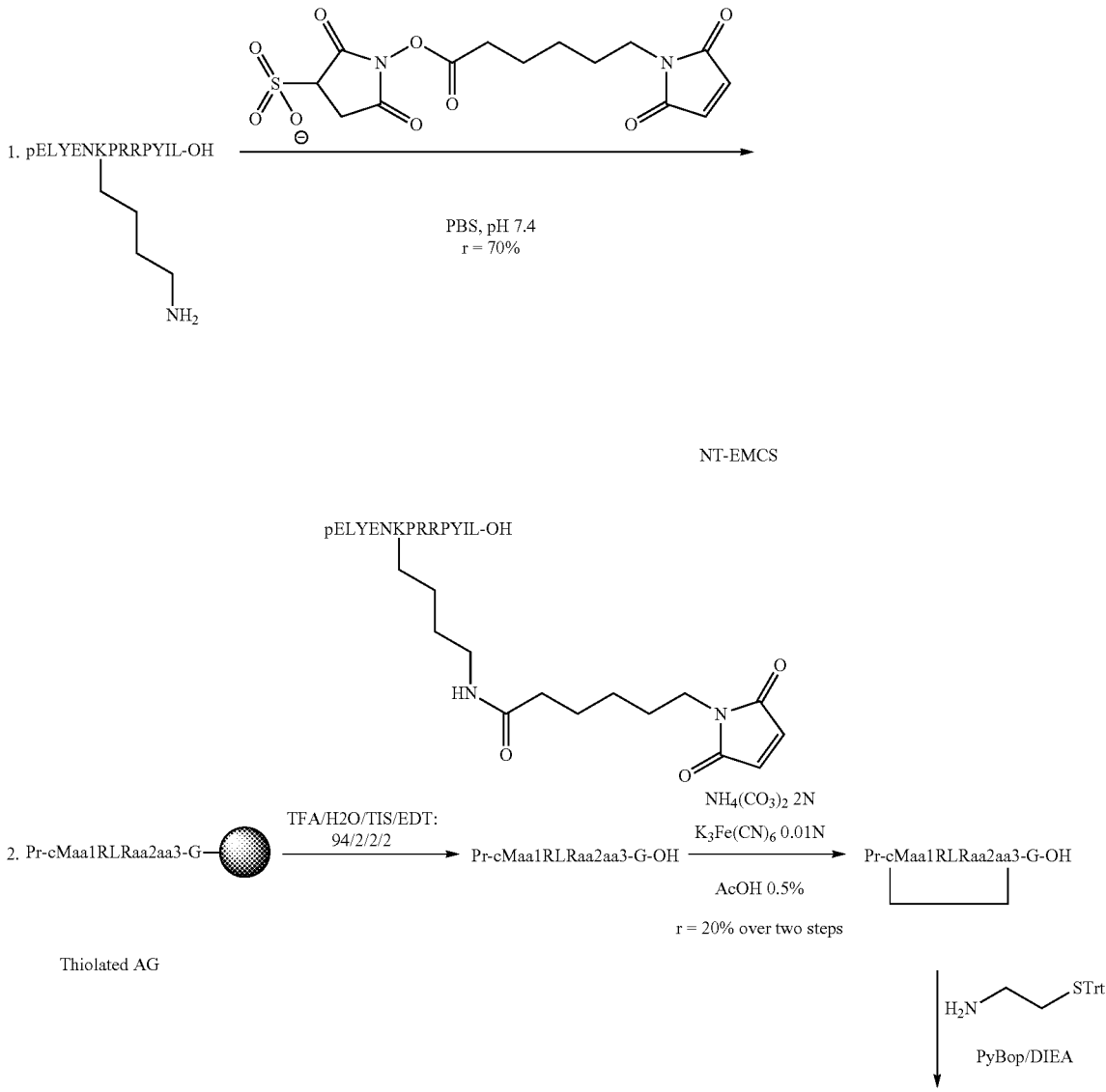

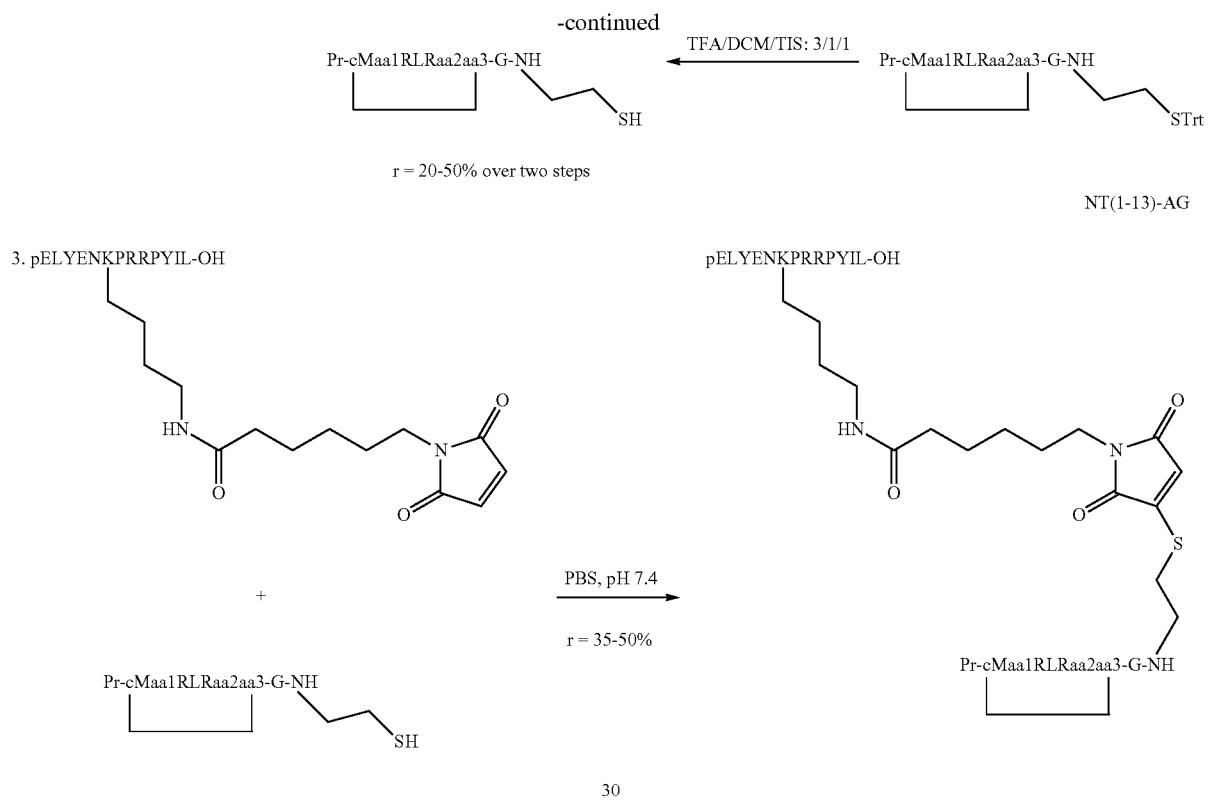

Analytical and Purification Methods:

Reaction progress and purity monitoring were carried out on a Dionex UltiMate® 3000 system equipped with a C18 Kinetex™ (5 µm, 150 mm×4.6 mm). Detection was done at 214 nm. Elution system was composed of $H_2O$/0.1% TFA (solution A) and MeCN/0.1% TFA (solution B). Flow rate was 2 mL/min with a gradient of 0-100% B in 4 min.

Crude products were purified by RP-HPLC on a Dionex UltiMate® 3000 system equipped with a C18 Luna™ (5 µm, 100 mm×21.2 mm). Detection was done at 214 nm. Elution system was composed of $H_2O$/0.1% TFA (solution A) and MeCN/0.1% TFA (solution B). Flow rate was 20 mL/min.

1. NT-EMCS synthesis

Full-size NT was purchased from Biochem AG while sulfo-EMCS (N-epsilon-Maleimidocaproyl-oxysulfosuccinimide ester) was purchased from Thermo Scientific (Pierce Biotechnology).

Functionalized NT-EMCS was prepared by adding a solution of sulfo-EMCS (9.2 mg, 15 µmol, 1 eq. in 1 mL of PBS 4×pH=7.4) to a solution of NT (25 mg, 15 µmol, 1 eq. in 1.25 mL PBS 4×pH=7.4). Reaction mixture was allowed to stir at room temperature. Monitoring of the reaction was performed by analytical RP-HPLC. After overnight stirring the crude mixture was purified by preparative RP-HPLC with a gradient of 21-30% B in 30 min. Fractions with purities above 95% were collected and lyophilized to give a pure white powder (m=21 mg, yield=75%, purity >95%). The mass was confirmed by MALDI-TOF MS analysis: m/z $[M+H]^+$ calculated 1865.98. found 1865.97.

2. Synthesis of Thiolated AG

For AG conjugation to the maleimide moiety of functionalized NT, a thiol reactive group was introduced on each candidate AG.

Synthesis of Peptides Pr-cMaa1RLRaa2aa3-G-OH

Peptides Pr-cMaa1RLRaa2aa3-G-OH were synthesized by the solid-phase peptide synthesis (SPPS) method on a Liberty™ (CEM) microwave synthesizer, using a Fmoc/tBu strategy and a Fmoc-Gly-Wang Resin (100-200 mesh, 1% DVB, loading 0.7 mmol/g) purchased from Iris Biotech. Such a resin allows synthesis of peptides completely deprotected on their side chains and their C-terminal ends.

N-α-Fmoc-protected amino acids were chosen with standard orthogonal side chain protections: Fmoc-Cys(Trt)-OH (in configuration D or L), Fmoc-Pen(Trt)-OH (in configuration D or L), Fmoc-Met-OH, Fmoc-Pro-OH, Fmoc-Pip-OH, Fmoc-Thz-OH, Fmoc-Arg(Pbf)-OH, Fmoc-Leu-OH, Fmoc-Gly-OH and Fmoc-Sar-OH. They were all purchased from Iris Biotech as well as piperidine, Trifluoroacetic acid (TFA), Diisopropylethylamine (DIEA), ethanedithiol (EDT), Triisopropylsilane (TIS), 2-(1H-benzotriazole-1-yl)-1,1,3,3-tetramethyluronium hexafluorophosphate (HBTU), and 1-[Bis(dimethylamino)methylene]-1H-1,2,3-triazolo[4,5-13]pyridinium 3-oxide hexafluorophosphate (HATU). Dimethylformamide (DMF), Dichloromethane (DCM) and propionic anhydride ($Pr_2O$) were purchased from Sigma-Aldrich.

Amino acids were coupled via microwave activation of the acid function of the n+1 amino acid using aa/DIEA/HBTU: 4/4/8 equivalent (with respect to the resin) in a 0.25 mmol scale synthesis and aa/DIEA/HBTU: 5/5/10 equivalent (respective to the resin) in a 0.1 mmol scale synthesis. Coupling time was adjusted to 10 min. Double couplings were necessary for methionine and cysteine incorporation after aa1 introduction. Deprotection of the Fmoc group of a new amino acid thus coupled was carried out using 20% piperidine in DMF. The last amino acid coupled during peptide elongation was propionylated or acetylated using 50% propionic anhydride or acetic anhydride in DCM. The aim of the N-terminal capping was to stabilize the synthesized neopeptide and also to reduce the risks of secondary reactions during covalent coupling in the C-terminal position, for example. In order to keep an N-terminus chemical structure similar to that of some radiolabeled peptides, which are occasionally labeled on the N-terminal amino group using a tritiated propionyl succinimide ester, a propionyl rather than an acetyl moiety was chosen. Resin-bound peptides were then cleaved using a solution comprised of TFA/TIS/H2O/EDT: 94/2/2/2 for at least 2 hours at room temperature (RT). A minimum of 15 mL of cleavage solution was used per gram of resin. Crude peptides were then precipitated using ice-cold ether, centrifuged at 3000 rpm for 8 min and lyophilized in $H_2O$/0.1% TFA. White solids were obtained and engaged in the next step without any further purification.

Cyclization of Peptides Pr-cMaa1RLRaa2aa3-G-OH

Disulfide bridges were obtained by intramolecular cyclization from two thiol functions of two suitably protected Cys or Pen, either in configuration L or D.

AcOH, $K_3[Fe(CN)_6]$ and ammonium carbonate were purchased from Sigma-Aldrich. Crude Pr-cMaa1RLRaa2aa3-G-OH peptides were dissolved in AcOH 0.5% to get a 0.5 mg/mL final concentration. Ammonium carbonate (2N) was added to the peptide solutions to reach an approximate basic pH of 8-9. $K_3[Fe(CN)_6]$ (0.01N) was then added to the reaction mixtures until a bright and persistent yellow color was observed. Monitoring of the reactions was performed by analytical RP-HPLC. Usually reactions were quantitative in less than 30 min. Reaction mixtures were filtered on a 0.45 µm membrane and purified by preparative RP-HPLC. Fractions with purities above 95% were collected and lyophilized to give pure white powders (final purity >95%). Detailed gradients, yields and mass analysis are given hereafter.

| Peptide | Gradient (% B in 30 min) | Yield | MS (exact/found) |
| --- | --- | --- | --- |
| SEQ ID NO: 8 | 14-24 | 12% | 1032.40/1032.42 |
| SEQ ID NO: 9 | 14-20 | 15% | 1074.49/1074.50 |
| SEQ ID NO: 10 | 15-25 | 20% | 1092.47/1092.47 |
| SEQ ID NO: 11 | 18-24 | 25% | 1101.52/1101.54 |

Cysteamine Coupling on Cyclized Pr-cMaa1RLRaa2aa3-G-OH Peptides

2-Tritylthio-1-ethylamine hydrochloride (Trt-cysteamine) was purchased from Iris Biotech while other reactants were purchased as already described above.

Solutions of Trt-cysteamine (2 eq.), DIEA (4 eq.) and cyclized peptides containing a free C-terminal (1 eq.) were prepared in anhydrous DMF (0.05M respective to the peptide). PyBop (1.1 eq, in anhydrous DMF 0.13M) was finally added to the mixtures. Completion of reactions was reached almost immediately as HPLC monitoring after 2 min showed complete disappearance of the starting peptides. DMF was evaporated under vaccum to yield a pale yellow oil. To remove the trityl thiol protection a solution of DCM/TIS/TFA: 3/1/1 was added (approximately 0.5 mL/mg of starting peptides). Reaction mixtures were allowed to stir at RT. Monitoring of the reactions was performed by analytical RP-HPLC. DCM and TFA were then evaporated using inert gas bubbling and $Et_2O$ made crude peptides precipitate. After centrifugation at 3000 rpm for 8 min crude peptides were lyophilized in $H_2O$/0.1% TFA and purified by preparative RP-HPLC. Fractions with purities above 95% were collected and lyophilized to give pure white powders (final purity >95%). Detailed gradients, yields and mass analysis are given hereafter.

| Peptide | Gradient (% B in 30 min) | Yield | MS (exact/found) |
| --- | --- | --- | --- |
| SEQ ID NO: 8-G-NH—CH$_2$—CH$_2$—SH | 12-22 | 66% | 1091.40/1091.44 |
| SEQ ID NO: 9-G-NH—CH$_2$—CH$_2$—SH | 19-29 | 43% | 1133.51/1133.54 |
| SEQ ID NO: 10-G-NH—CH$_2$—CH$_2$—SH | 20-30 | 56% | 1152.47/1152.63 |
| SEQ ID NO: 11-G-NH—CH$_2$—CH$_2$—SH | 19-27 | 58% | 1161.54/1161.56 |

3. NT(1-13)-AG Synthesis by NT-EMCS Conjugation to Thiolated AGs

AGs containing a thiol reactive group were solubilized in PBS 1× (1 eq., 0.003M, pH 7.4) and added to NT-EMCS (1 eq). Reaction mixtures were allowed to stir at RT. Usually ultrasonic waves helped to solubilize NT-EMCS. Monitoring of the reactions was performed by analytical RP-HPLC. After reaction completion crude products were purified by preparative RP-HPLC. Fractions with purities above 95% were collected and lyophilized to give pure white powders (final purity >95%). Detailed gradients, yields and mass analysis are given hereafter.

| Molecule | Compound | Gradient (% B in 30 min) | Yield | MS (exact/found) |
|---|---|---|---|---|
| NT-SEQ ID NO: 8 | I | 18-27 | 39% | 2958.52/2958.45 |
| NT-SEQ ID NO: 9 | II | 21-31 | 40% | 2998.50/2998.57 |
| NT-SEQ ID NO: 10 | III | 20-30 | 40% | 3016.45/3016.62 |
| NT-SEQ ID NO: 11 | IV | 21-32 | 39% | 3026.53/3026.59 |

Example 2

In Vitro Binding Affinity of Activated NT Drugs of the Invention

The central hypothermic effects of neurotensin are mediated through activation of the NTR-1 receptor. In order to elicit biological activity such as hypothermic activity, neurotensin conjugates should bind the NTR-1 with at least a similar affinity to that of native neurotensin, namely NT(1-13).

The binding affinity of the neurotensin conjugates was assessed using a competition binding assay with both human and rat neurotensin receptor type 1 (hNTR-1, rNTR-1). The cell membranes enriched for the hNTR-1 were purchased from PerkinElmer. Rat NTR-1 was obtained by transfecting HEK293 cells with a rat NTSR1 plasmid construct (Origene, Rockville, USA).

The binding affinity of activated NT drugs on hNTR-1 was performed according to the manufacturer's instructions (PerkinElmer) with slight modifications. In detail, NTR-1 binding was measured using membrane homogenates, prepared from CHO cells stably expressing human NTR-1, at a final concentration of 0.5 μg/well and the radioligand [$^3$H]-neurotensin (specific activity 99.8 Ci·mmol$^{-1}$; PerkinElmer) at a concentration of 3 nM. Specific binding of the radioligand was determined with $K_D$ values of 0.81 nM and a $B_{max}$ of 34 pmol per mg membrane protein. Nonspecific binding was determined in the presence of 5 μM neurotensin.

For assays with rat neurotensin receptor type 1 (rNTR1), we used the membrane homogenates from HEK293 cells expressing rNTR-1 at a final concentration of 0.75 μg/well. Specific binding of the radioligand on these homogenates was determined at $K_D$ values of 0.93 nM and a $B_{max}$ of 2.5 pmol per mg membrane protein.

Each assay was performed in a 96-well plate in a total reaction volume of 100 μL in binding buffer (50 mM Tris-HCl, pH 7.4, 0.1% BSA). The assay was subsequently incubated for 24 h at room temperature. The content of each well was rapidly filtered through Unifilter®-96, GF/C® filters (PerkinElmer, presoaked with 25 μL of 0.5% polyethylenimine) using a MicroBeta FilterMate-96 Harvester (PerkinElmer) and each well was then rinsed 5 times with washing buffer (10 mM Tris-HCl, pH 7.2). Radioactivity (cpm) of each dried filter was measured by adding 25 μL of MicroScint™-O (PerkinElmer) and quantified using Top-Count NXT™ Microplate Scintillation and Luminescence Counter (PerkinElmer). Specific binding was typically 90% or greater of the total binding. Dose-response curves were plotted using KaleidaGraph to determine $IC_{50}$ values. Assays were performed in duplicate. Ki values were determined from mean $IC_{50}$s using the Cheng-Prusoff conversion.

| Compound | Formula | NTR-1 binding affinity Ki (nM) | |
|---|---|---|---|
| | | Human NTR-1 | Rat NTR-1 |
| | NT(1-13) | 0.82 ± 0.50 | 0.34 ± 0.08 |
| | NT(8-13) | 0.05 ± 0.01 | 0.12 ± 0.04 |
| IX | SEQ ID NO: 9-NT(8-13) | 0.09 ± 0.04 | 0.03 ± 0.02 |
| X | SEQ ID NO: 9-GGG-NT(8-13) | 0.13 ± 0.07 | ND |
| XIV | SEQ ID NO: 9-PEG6-NT(8-13) | 0.22 ± 0.06 | 1.06 ± 0.47 |
| XV | [Tle12]NT(8-13) | 0.20 ± 0.10 | 0.43 ± 0.12 |
| | SEQ ID NO: 9-[Tle12]NT(8-13) | 0.40 ± 0.20 | 0.06 ± 0.02 |
| XVI | [Lys8, Tle12]NT(8-13) | 0.22 ± 0.05 | 0.68 ± 0.59 |
| | SEQ ID NO: 9-[Lys8, Tle12]NT(8-13) | 0.15 ± 0.06 | 0.12 ± 0.06 |
| XVII | [Lys9, Tle12]NT(8-13) | 1.70 ± 0.40 | 4.20 ± 1.60 |
| | SEQ ID NO: 9-[Lys9, Tle12]NT(8-13) | 0.47 ± 0.19 | 0.19 ± 0.07 |
| XVIII | [Trp11, Tle12]NT(8-13) | 3.10 ± 1.50 | 0.85 ± 0.29 |
| | SEQ ID NO: 9-[Trp11, Tle12]NT(8-13) | 2.98 ± 1.08 | 0.02 ± 0.01 |
| XIX | [Lys8, Trp11, Tle12]NT(8-13) | 13.80 ± 2.90 | 3.31 ± 1.26 |
| | SEQ ID NO: 9-[Lys8, Trp11, Tle12]NT(8-13) | 6.34 ± 2.25 | 0.03 ± 0.02 |
| XX | SEQ ID NO: 11-[Lys8, Tle12]NT(8-13) | 0.11 ± 0.03 | 0.08 ± 0.06 |

ND: Not determined

These results show that the activated molecules of the invention retain very high affinity for NTR-1, in the nanomolar range or even below. In fact, in most cases, the AG increased significantly the affinity of the different NT drugs for NTR-1. Such results are remarkable and unexpected since conjugation may rather be expected to interfere negatively with receptor binding.

Example 3

In Vivo Evaluation of Activated NT Drugs of the Invention

The beneficial effect of the activated NT drugs of the invention on the central pharmacological activity of neurotensin was investigated by monitoring the hypothermic response in Swiss (CD-1) mice (FIG. 1). Following intravenous (bolus) administration of NT at 8 mg/kg, mice showed a minor but significant decrease in rectal body temperature, with a maximal effect of −1° C. from baseline at 15 min post-injection. This effect increased at 24 mg/kg, reaching a maximal effect of −2.6° C. at 30 min post-injection. By contrast, intravenous administration of compound I, an activated NT drug of the invention comprising SEQ ID NO: 8 as an activator group, at the molar equivalent dose of 8 mg/kg (8 mg/kg eq. NT) induced a rapid and stronger decrease in body temperature, significant as of 15 min post-injection and reaching a maximal effect of −3.7° C. between 30 and 60 min post-injection. This pharmacological hypothermia progressively decreased thereafter until returning to baseline temperature within 3 hours post-injection. No shivering was observed in these mice during the course of the experiment.

Evaluation of lower dose levels for compound I showed a dose-dependent hypothermic effect, with a Minimal Effective Dose (MED) of 0.5 mg/kg eq. NT, an $ED_{50}$ of 1.21 mg/kg eq. NT and a maximal effect of about −4° C. observed as of 4 mg/kg eq. NT with no stronger effect at 8 mg/kg eq. NT (FIG. 2). The time to reach the maximal effect increased with higher dose levels, from 15 min post-injection at low dose levels to 30-60 min post-injection at high dose levels. When compared to NT alone, which displays an MED of 8 mg/kg, this activated NT drug showed a 16-fold increase in the central hypothermic effect.

Alternative activating groups (AGs) according to the invention were then tested. When compared to compound I at the same dose-level of 0.5 mg/kg eq. NT, activated NT drugs comprising, for example, SEQ ID NO: 9 or SEQ ID NO: 11 as activator groups, namely compound II (NT-SEQ ID NO: 9) and compound IV (NT-SEQ ID NO: 11), induced an even greater hypothermic response in mice, with a maximal effect of −4.1° C. and −3.4° C., respectively, at 30 min post-injection (FIG. 3). Compound II was selected for further investigation.

Evaluation of the dose-response relationship of compound II demonstrated an MED of 0.1 mg/kg eq. NT, which is 80-fold lower than NT alone, and $ED_{50}$ of 1.25 mg/kg eq. NT (FIG. 4). At high dose levels, compound II induced an even stronger hypothermia, reaching a maximal effect of −7° C. at 60 min post-injection at 10 mg/kg eq. NT. At this high dose level, mice showed a reduced locomotor activity that timely paralleled the hypothermic effect, but remained fully responsive to different kinds of stimuli. Again, no shivering was observed even in mice displaying body temperatures around 30° C.

Example 4

BBB-Transport of Activated NT Drugs of the Invention

We evaluated the BBB-permeability and in vitro blood stability of activated neurotensin drugs of the invention.

Transport kinetics at the BBB and blood-retina barrier (BRB) of the conjugates of the invention was assessed using an in situ brain perfusion technique in adult male C57Bl/6 mice. Radiolabeled activated NT compounds were obtained either by coupling [3H]Tyr3-NT with the AG or by coupling a tritiated AG to NT molecules. NT was radiolabeled by catalytic dehalogenation of iodoTyr3-NT using tritium gas while AG was radiolabeled by coupling a tritiated propionyl succinimide ester to its N-terminus. The specific radioactivity (SRA) was typically in the range of 50 Ci/mmol. The total quantity of radioactivity prepared for each synthesis was generally between 100 and 1000 µCi.

The in situ brain perfusion technique enables total control of the composition of the artificial perfusate in order to maintain the cells and vascularization of the brain under normal physiological and anatomical conditions within the animal, without the disrupting factor of systemic distribution. In situ brain perfusion was initially developed in the rat and was adapted for the mouse by Dagenais et al. (2000, J. Cereb. Blood Flow Metab., 20(2):381-6). This allows evaluation of the transport kinetics of compounds across the BBB and BRB in transgenic and KO mutant mice for receptors of interest, enzymes or different kinds of influx or efflux transporters.

In situ brain perfusion of the radiolabeled compounds of the invention was performed during 120 s with a perfusate flow rate of 2 mL/min. The initial transport was expressed as the transfer coefficient $K_{in}$ (relationship between distribution volume of the test compound, corrected for the vascular volume, and cerebral perfusion time). Co-perfusion of radiolabeled sucrose, a compound that does not normally cross the BBB, also allowed assessment of the physical integrity of the BBB and hence the absence of acute toxicity of the test compound.

Consistently with data found in the literature, NT demonstrated a very low initial transport in the brain, with a Kin value of ~0.4×10-4 mL/s/g brain tissue. NT transport in the eye was even lower (FIG. 5, white bars). Importantly, the results obtained with the radiolabeled activated NT drugs of the invention consistently showed significantly higher transport kinetics into the brain and the eye, demonstrating that activation of NT with an activator group of the invention specifically enhanced its transport into these otherwise non-permeable organs. In particular, compound XIV showed a Kin value in the brain of ~3.65×10-4 mL/s/g, which is a 9-fold increase when compared to free NT, and ~32.0×10-4 mL/s/g in the eye (FIG. 5, black grey bars). Furthermore, compound I did not alter the integrity of the BBB since the brain distribution volume of sucrose was similar to control values.

Example 5

In Vitro Stability of Activated NT Drugs of the Invention

In vitro blood stability (half-life or $t_{1/2}$) of the drugs of the invention was assessed and compared to that of NT alone. Briefly, each peptide was incubated at the nominal concentration of 2 µM up to 3 hours at 37° C. in freshly collected Swiss (CD-1) mouse blood. The analyte was quantified in the plasma fraction at several time points using a liquid chromatography-tandem mass spectrometry (LC-MS/MS) analytical method. In vitro half-life ($t_{1/2}$) was estimated from the logarithmic regression of each kinetic profiles (first-order reaction kinetics: $C(t)=C_0 \cdot e^{-kt}$) and given by $t_{1/2}=\ln 2/k$.

The results confirmed the very low resistance of native NT to plasma degradation, with an in vitro half-life of only 7 min (FIG. 6). This is consistent with the rapid enzymatic proteolysis of endogenous peptides and generally small linear peptides containing only natural amino acids (Foltz et al., January 2010, *J. Nutr.*, 140(1):117-8). In sharp contrast, all activated NT drugs of the invention showed a greatly enhanced $t_{1/2}$ in mouse blood, typically over 1 hour.

| Test Molecules | Compound | Reaction rate constant k ($h^{-1}$) | In vitro half-life (min) |
|---|---|---|---|
| NT | — | 5.779 | 7 |
| NT-SEQ ID NO: 8 | I | 0.813 | 51 |
| NT-SEQ ID NO: 11 | IV | 0.419 | 100 |

Taken together, the BBB-transport kinetics, the in vitro stability in blood, and the enhanced central hypothermic effect demonstrate the remarkable and unexpected beneficial effects of activated NT drugs of the invention.

Example 6

Synthesis of NT(x-13)-Based Activated Neurotensin Molecules

Examples 1-5 showed that SEQ ID NO: 9 was particularly effective in activating full-size NT. In the present and following examples, SEQ ID NO: 9 was tested for its ability to generate potent activated neurotensin molecules based on NT fragments.

It is reported in the literature that some truncated neurotensin analogs are as potent as the full-length endogenous neuropeptide, especially when the minimal sequence corresponding to amino acids 8-13 is present. On this basis new activated NT drugs were prepared using NT analogs having a reduced size, with the objectives of generating more potent drugs while minimizing the production costs and allowing tandem conjugation on the N-terminal part of NT.

Conjugates were synthesized with the same conjugation method employed for those comprising full-size neurotensin (see Example 1), with a focus on three neurotensin fragments: NT(2-13), where only pyroglutamic acid is missing, and NT(6-13) and Lys-NT(8-13), comprising the minimal active sequence and further containing at least lysine 6, used for coupling to the AG. Analytical and purification methods were performed as described in Example 1.

1. NT(x-13) Peptide Synthesis

Truncated neurotensin analogs were synthesized by the solid-phase peptide synthesis (SPPS) method on a Liberty™ (CEM) microwave synthesizer, using a Fmoc/tBu strategy. Amino acid coupling was performed from a manually preloaded Fmoc-Leu-Wang Resin (100-200 mesh, 1% DVB). Such a resin allows synthesis of peptides completely deprotected on their side chains and their C-terminal ends.

Wang resin (loading 0.2 mmol/g) was purchased from Iris Biotech. Other raw materials were already described before. For resin preloading, a solution of Fmoc-Leu-OH/HOBt/DIC (6 eq./6 eq./6 eq.) in DMF (0.055M respective to the aa) was added to the resin. DMAP (1 eq.) was then added. After overnight mechanical stirring, the resin was washed and its loading was evaluated. Usually loading was comprised between 0.1 and 0.16 mmol/g.

Peptide elongation was performed as already described. Peptide N-termini were acetylated using 50% acetic anhydride in DCM to mimic the peptide bonds found in the endogenous peptide and to increase metabolic stability. Resin-bound peptides were cleaved with the same procedure as previously described and purified by RP-HPLC. Fractions with purities above 95% were collected and lyophilized to give pure white powders (final purity >95%). Detailed gradients, yields and mass analysis are given hereafter.

| Peptide | Gradient (% B in 30 min) | Yield | MS (exact/found) |
|---|---|---|---|
| NT(2-13) | 19-29 | ND | 1603.89/1603.72 |
| NT(6-13) | No purification | ND | 1084.66/1084.44 |
| Lys-NT(8-13) | 16-26 | 27% | 987.6/987.635 |

ND: Not Determined

2. NT(x-13)-EMCS Synthesis

NT(x-13) functionalization was performed with the same procedure as for full-size NT described in Example 1. Peptides were generated as pure white powders with a purity of at least 95%. Detailed gradients, yields and mass analysis are given hereafter.

| Peptide | Gradient (% B in 30 min) | Yield | MS (exact/found) |
|---|---|---|---|
| NT(2-13)-EMCS | 30-40 | 51% | 1796.96/1796.39 |
| NT(6-13)-EMCS | 20-34 | 24% | 1277.51/1277.74 |
| Lys-NT(8-13)-EMCS | 17-27 | 20% | 1180.68/1180.67 |

3. Synthesis of Thiolated SEQ ID NO: 9

Thiolated SEQ ID NO: 9 was synthesized as described in Example 1.

4. Synthesis of Conjugates NT(x-13)-SEQ ID NO: 9

NT(x-13)-EMCS coupling procedure to SEQ ID NO: 9 was the same as for NT(1-13)-AG synthesis as detailed in Example 1. Conjugates were generated as pure white powders with a purity of at least 95%. Detailed gradients, yields and mass analysis are given hereafter.

| Peptide | Compound | Gradient (% B in 30 min) | Yield | MS (exact/found) |
|---|---|---|---|---|
| NT(2-13)-SEQ ID NO: 9 | V | 30-40 | 43% | 2929.47/2929.69 |
| NT(6-13)-SEQ ID NO: 9 | VI | 30-40 | 46% | 2410.24/2410.38 |
| Lys-NT(8-13)-SEQ ID NO: 9 | VII | 25-40 | 42% | 2313.19/2313.24 |

Example 7

Hypothermic Response of Activated NT(x-13) Drugs of the Invention

The hypothermic response of the activated drugs was assessed by intravenous (bolus) injection in Swiss (CD-1) mice of each conjugate at the same dose level of 0.5 mg/kg eq. NT.

All truncated NT-based drugs induced a similar degree of hypothermia in mice with a maximal decrease in body temperature of about −2.5° C. at 30 min post-injection (FIG. 7). These results show that the shortest C-terminal NT(8-13) fragment is sufficient to elicit a potent biological activity in the context of the activated drugs of the invention.

Example 8

Synthesis of Activated NT Drug Conjugates Using Disulfide Bridging

Activated NT drug conjugates of the invention described in Examples 1 and 4 were synthesized using an EMCS linker and a lysine residue naturally found or introduced in the NT sequence. In an attempt to evaluate new linking strategies, NT(8-13) and SEQ ID NO: 9 were conjugated via a disulfide bridge. Such a cleavable linker exhibits a good stability in systemic circulation while it can be cleaved in the reducing environment of some intracellular compartments, particularly in endothelial cells of the BBB, potentially leading to the release of fully active NT (8-13) in brain parenchyma. Moreover, changing the linker results in a new drug with distinct and potentially beneficial PK, disposition and metabolism properties.

Disulfide bridges are made from two thiol groups naturally present or introduced on both moieties to be conjugated. In the context of the invention the two moieties to be conjugated presented no free cysteine, and hence two thiol functions were chemically introduced on AG and NT. For this purpose, a cysteine residue protected by the thiol-activating Npys was introduced at the N-terminus of NT(8-13). Npys-derivatized Cys is specifically reactive toward free thiols and hence favors formation of the heterodisulfide bridge. The thiolated SEQ ID NO: 9 was generated by C-terminal functionalization with cysteamine in the same manner as for conjugation to NT-EMCS. Both moieties were produced independently and then conjugated to each other in a final step. The coupling steps are schematically represented below:

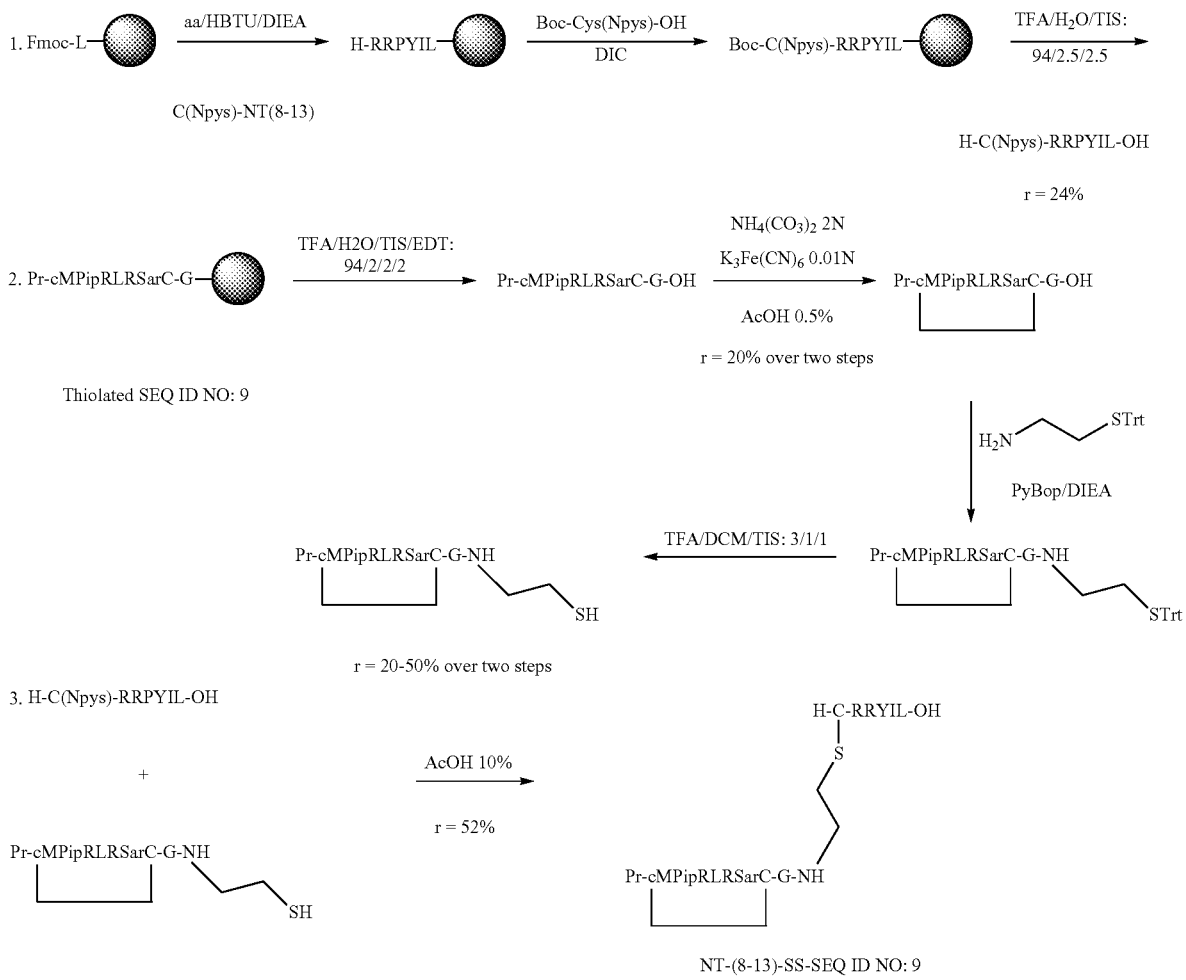

Analytical and purification methods are as described in Example 1.

1. Synthesis of Peptide C(Npys)-NT(8-13)

Boc-Cys(Npys)-OH and DIC (diisopropylcarbodiimide) were purchased from Iris Biotech.

H-NT(8-13) was prepared as described in Example 6 except the N-terminus was not capped. A solution of Boc-Cys(Npys)-OH (5 eq.) and DIC (5 eq.) in anhydrous DMF (0.33M) was pre-activated for 10 min at RT and added to the resin. After overnight mechanical stirring the resin was washed with DMF and DCM and the resin-bound peptide was cleaved and treated using the same procedure described in the previous examples. Purification of the crude peptide with a gradient of 17-26% B in 30 min led to a pure pale yellow powder (m=25.9 mg, yield=24%, purity >95%). The mass was confirmed by MALDI-TOF MS analysis: m/z [M+H]$^+$ calculated 1074.49. found 1074.47. As the Npys protection was cleaved in MALDI-TOF during analysis, the product without this group was also observed: [M-Npys+H+H]$^+$ calculated 920.51. found 920.475.

2. Synthesis of Thiolated SEQ ID NO: 9

Thiolated SEQ ID NO: 9 was produced as disclosed in Example 1.

3. Synthesis of Activated NT Conjugate NT(8-13)-SS-SEQ ID NO: 9 (Compound VIII)

C(Npys)-NT(8-13) (1.3 eq.) was dissolved in a degassed 10% acetic acid solution under inert atmosphere (0.02M). Thiolated SEQ ID NO: 9 (1 eq.) was dissolved in a degassed 10% acetic acid solution under inert atmosphere (0.015M) and immediately added to the C(Npys)-NT(8-13) solution. The reaction mixture was allowed to stir at RT under inert atmosphere. Monitoring of the reactions was performed by analytical RP-HPLC. After 48 hours stirring C(Npys)-NT(8-13) (0.45 eq.) was again added to the reaction mixture. After completion of the reaction, purification of the crude mixture was performed by preparative RP-HPLC with a gradient of 17-27% B in 30 min. A pure white powder was obtained (m=7.8 mg, yield=52%, purity >95%). The mass was confirmed by MALDI-TOF MS analysis: m/z [M+H]$^+$ calculated 2050.00. found 2051.08.

Example 9

Hypothermic Response of NT(8-13)-SS-SEQ ID NO: 9 Activated Drug Conjugate

The hypothermic response of NT(8-13)-SS-SEQ ID NO: 9 (compound VIII) was assessed by intravenous (bolus) injection in Swiss (CD-1) mice at the dose level of 10 mg/kg eq. NT and compared to that of the drug obtained using cysteamine-EMCS linker, namely compound II.

Compound VIII induced a potent hypothermia in mice, to a similar extent than compound II. Both compounds induced a maximal decrease in body temperature of −5.8° C. at 45 min post-injection and −6.7° C. at 1 hr, respectively (FIG. 8). Thus, coupling of NT(8-13) using a disulfide linker appears as an adequate strategy to activate NT while presumably allowing the release of NT in reducing environments such as brain capillary endothelial cells.

Example 10

Synthesis of Tandem AG-NT Activated Drugs

The activated NT drugs disclosed in the previous examples were synthesized by independent preparation and functionalization of the NT and AG moieties followed by their coupling. In the present example, a new series of activated NT drugs was produced using tandem synthesis and SPPS-compatible spacers. Alternatively, the NT and AG moieties are coupled directly by means of a peptide bond. Synthesis of such drugs can be performed in tandem with only two steps: peptide elongation on support and AG disulfide bond formation. Using this strategy, activated NT drugs based on the most preferred NT(8-13) fragment and analogs thereof have been prepared with an overall yield up to 35%. Furthermore, tandem synthesis allows the use of many linkers as spacers between the AG moiety and the NT polypeptide. Importantly, the NT polypeptide was introduced at the C-terminus of the conjugate, since a free carboxyl terminus is essential for binding to NT receptors. Among these common linkers are amino acid-based linkers such as triglycine. Aminohexanoic acid was also chosen. This non-natural amino acid is a common hydrophobic linker used to increase the distance between a peptide and another moiety. Finally two PEG spacers were also evaluated to make the conjugate more hydrophilic and hence more water-soluble and biologically tolerant. Two PEG molecules were tested to assess the impact of the distance between the AG and the NT polypeptide on its biological activity. All linkers/spacers introduced in the drug conjugates provided flexibility to the drug, which is important for optimal recognition of the target receptor by the NT polypeptide. Analytical and purification methods were performed as described in Example 1.

1. Synthesis of SEQ ID NO: 9-NT(8-13), SEQ ID NO: 9-GGG-NT(6-13), SEQ ID NO: 9-Ahx-NT(6-13) and SEQ ID NO: 9-Ahx-NT(8-13)

Compound IX (SEQ ID NO: 9-NT(8-13), compound X (SEQ ID NO: 9-GGG-NT(6-13)), compound XI (SEQ ID NO: 9-Ahx-NT(6-13)) and compound XII (SEQ ID NO: 9-Ahx-NT(8-13)) were synthesized by the solid-phase peptide synthesis (SPPS) method on a Liberty™ (CEM) microwave synthesizer, using an Fmoc/tBu strategy and an Fmoc-Leu-Wang Resin (100-200 mesh, 1% DVB, loading 0.09 mmol/g) manually preloaded as described above.

Fmoc-Ahx-OH was purchased from Iris Biotech. Other raw materials were already described above.

Peptide elongation, cleavage and treatment were performed using the same procedure as described in previous examples. Double coupling was performed for D-Cys, Met, and NT-Arg9 amino acids. Peptide N-termini were propionylated using 50% propionic anhydride in DCM. Crude peptide SEQ ID NO: 9-GGG-NT(6-13) was purified by preparative RP-HPLC with a gradient of 15-25% B in 30 min. Crude peptides comprising either no spacer (only peptide bond) or an Ahx spacer were used without further purification in the next cyclization step.

Disulfide bridges were obtained by intramolecular cyclization from the two cysteines contained in the AG (positions 1 and 8) using the same protocol as the one detailed in Example 1. Pure drugs were obtained as white powders (final purity >95%). Detailed gradients, yields and mass analysis are given hereafter.

| Peptide | Compound | Gradient (% B in 30 min) | Yield | MS (exact/found) |
|---|---|---|---|---|
| SEQ ID NO: 9-NT(8-13) | IX | 18-28 | 7% | 1815.96/1815.92 |
| SEQ ID NO: 9-GGG-NT(6-13) | X | 17-25 | 4% | 2212.17/2212.10 |
| SEQ ID NO: 9-Ahx-NT(6-13) | XI | 19-28 | 4% | 2154.19/2154.11 |
| SEQ ID NO: 9-Ahx-NT(8-13) | XII | 17-27 | 21% | 1929.04/1929.00 |

2. Synthesis of SEQ ID NO: 9-PEG2-NT(8-13) and SEQ ID NO: 9-PEG6-NT(8-13)

Compound XIII (SEQ ID NO: 9-PEG2-NT(8-13)) and compound XIV (SEQ ID NO: 9-PEG6-NT(8-13)) were synthesized by the solid-phase peptide synthesis (SPPS)

method on a Liberty™ (CEM) microwave synthesizer, except for the PEG spacer which was introduced manually. An Fmoc/tBu strategy and an Fmoc-Leu-Wang Resin (100-200 mesh, 1% DVB, loading 0.09 mmol/g) manually pre-loaded as described before were used.

Fmoc-12-amino-4,7,10-trioxadodecanoic acid (Fmoc-PEG2-OH) and Fmoc-21-amino-4,7,10,13,16,19-hexaoxa-heneicosanoic acid (Fmoc-PEG6-OH) were purchased from PolyPeptide Laboratories. Other raw materials were already described above.

Peptide elongation was performed as previously described with the microwave Liberty™ synthesizer until PEG introduction and after its manual introduction. A double coupling was performed for D-Cys, Met, and NT-Arg9 amino acids. For manual coupling, PEG amino acids (2 eq.) were pre-activated with COMU (2 eq.) and DIEA (4 eq.) in anhydrous DMF (0.2M respective to the PEG) for 5 min. Activated PEGs were then added to the resin and the mixture was allowed to mechanically stir overnight at RT. Peptide N-termini were propionylated using 50% propionic anhydride in DCM. After cleavage and treatment as usual, crude peptides were used without further purification in the next cyclization step.

Disulfide bridges were obtained by intramolecular cyclization from the two cysteines contained in the AG in positions 1 and 8 with the same protocol as described in Example 1. Pure conjugates were obtained as white powders (final purity >95%). Detailed gradients, yields and mass analysis are given hereafter.

| Peptide | Compound | Gradient (% B in 30 min) | Yield | MS (exact/found) |
|---|---|---|---|---|
| SEQ ID NO: 9-PEG2-NT(8-13) | XIII | 21-31 | 35% | 1962.03/1961.25 |
| SEQ ID NO: 9-PEG6-NT(8-13) | XIV | 22-32 | 17% | 2151.15/2151.50 |

3. Synthesis of SEQ ID NO: 9-[Tle12]NT(8-13), SEQ ID NO: 9-[Lys8, Tle12]NT(8-13), SEQ ID NO: 9-[Lys9, Tle12]NT(8-13), SEQ ID NO: 9-[Trp11, Tle12]NT(8-13), SEQ ID NO: 9-[Lys8, Trp11, Tle12]NT(8-13) and SEQ ID NO: 11-[Lys8, Tle12]NT(8-13)

Compound XV (SEQ ID NO: 9-[Tle12]NT(8-13)), compound XVI (SEQ ID NO: 9-[Lys8, Tle12]NT(8-13)), compound XVII (SEQ ID NO: 9-[Lys9, Tle12]NT(8-13)), compound XVIII (SEQ ID NO: 9-[Trp11, Tle12]NT(8-13)), compound XIX (SEQ ID NO: 9-[Lys8, Trp11, Tle12]NT(8-13)) and compound XX (SEQ ID NO: 11-[Lys8, Tle12]NT(8-13)) were synthesized as described for compound IX (SEQ ID NO: 9-NT(8-13)) by the solid-phase peptide synthesis (SPPS) method on a Liberty™ (CEM) microwave synthesizer, using an Fmoc/tBu strategy and an Fmoc-Leu-Wang Resin (100-200 mesh, 1% DVB, loading 0.09 mmol/g) manually preloaded as described above.

Fmoc-Lys-OH, Fmoc-Trp-OH, and Fmoc-Tle-OH were purchased from Iris Biotech. Other raw materials were already described above.

Peptide elongation, cleavage and treatment were performed using the same procedure as described in previous examples. Double coupling was performed for D-Cys, Met, and NT-Arg9 amino acids. Peptide N-termini were propionylated using 50% propionic anhydride in DCM. After cleavage and treatment as usual, crude peptides were used without further purification in the next cyclization step.

| Peptide | Compound | Gradient (% B in 30 min) | Yield | MS (exact/found) |
|---|---|---|---|---|
| SEQ ID NO: 9-[Tle12]NT(8-13) | XV | 20-30 | 6% | 1815.96/1816.03 |
| SEQ ID NO: 9-[Lys8, Tle12]NT(8-13) | XVI | 20-30 | 26% | 1787.95/1787.96 |
| SEQ ID NO: 9-[Lys9, Tle12]NT(8-13) | XVII | 20-30 | 19% | 1787.95/1787.91 |
| SEQ ID NO: 9-[Trp11, Tle12]NT(8-13) | XVIII | 23-33 | 5% | 1838.97/1838.94 |
| SEQ ID NO: 9-[Lys8, Trp11, Tle12]NT(8-13) | XIX | 24-34 | 10% | 1810.97/1811.03 |
| SEQ ID NO: 11-[Lys8, Tle12]NT(8-13) | XX | 20-30 | 22% | 1788.27/1786.95 |

Example 11

Hypothermic Response of Tandem AG-NT Activated Drugs

In order to determine the hypothermic effect of activated NT drugs obtained using a tandem synthesis procedure, each drug as well as compound II were injected intravenously (bolus) in Swiss (CD-1) mice at 10 mg/kg eq. NT and the rectal body temperature was monitored over 3 hours post-injection.

All drugs tested induced a potent and similar hypothermic response in mice, with comparable maximal decrease in body temperature and kinetics, reaching about −6/−7° C. at 60 min post-injection (FIG. 9).

Compound XIV displayed the best tolerance profile while exhibiting a strong hypothermic effect at this dose level, reaching −6.7° C. at 60 min post-injection. The $ED_{50}$ of compound XIV was 1.53 mg/kg eq. NT, which is similar to that measured for compound I and compound II. When compared to compound I, compound XIV showed an increased Kin in the brain and the eye, reaching 3.65×10-4 mL/s/g and 3.30×10-4 mL/s/g, respectively (FIG. 5, black bars) and a higher blood stability, with an estimated half-life of 96 min (FIG. 6). When injected at 20 mg/kg eq. NT in mice, compound XIV was still well-tolerated with no additional safety concerns. No further decrease in body temperature was observed at this dose level, indicating that the pharmacological hypothermic response saturated as of 10 mg/kg eq. NT. The Maximal Tolerated Dose (MTD) was 40 mg/kg eq. NT and the $LD_{50}$ (Lethal Dose, 50%) was not reached (>40 mg/kg eq. NT). Given that the MED was about 0.1 mg/kg eq. NT, this pharmacodynamic/toxicity profile constitutes an excellent safety prerequisite since i) it prevents potentially lethal overdose due to exacerbated pharmacological hypothermia, and ii) using the intravenous (bolus) mode of administration, the therapeutic window, which is expressed as the fold increase between the MED and MTD, is about 400, with 4-fold security between the dose level eliciting a maximal hypothermic response and that inducing mild/non-lethal toxicity.

Example 12

Hypothermic Response of Tandem Activated Drugs Comprising Substituted NT

In order to determine the hypothermic effect of activated NT drugs containing substituted versions of NT(8-13) obtained using a tandem synthesis procedure, each drug as well as the non-substituted compound IX were injected intravenously (bolus) in Sprague-Dawley rats at 5 mg/kg eq. NT and the rectal body temperature was monitored over 3 hours post-injection.

All drugs comprising stabilizing substitutions in the NT(8-13) sequence induced a higher hypothermic response in rats when compared to the non-substituted compound IX (FIG. 10). Maximal decrease in body temperature at 5 mg/kg eq. NT was −1.2° C. at 30 min post-injection for compound IX, around −2° C. at 60 to 90 min post-injection for compounds XV, XVI, XVII and XX and around −2.8° C. at 90 min post-injection for compounds XVIII and XIX.

Example 13

Repeated Administration of Activated NT Drugs of the Invention

In order to determine the hypothermic responsiveness of mice upon repeated administrations of activated NT of the invention, Swiss (CD-1) mice were challenged to four daily intravenous (bolus) administrations of compound XIV at 4 mg/kg eq. NT. Rectal body temperature was monitored each day during 3 hours post-injection.

On day 1, mice typically showed a maximal decrease in body temperature of −5.5° C. at 45 min post-injection (FIG. 11). Although the hypothermic response was slightly lower at day 2, the effect remained significant and stable thereafter (from day 2 to day 4), with a mean decrease in body temperature of −3° C. at 30 min post-injection.

Contrary to stable NT analogs that show no effect upon 3 days of repeated administration (Boules et al., 2003, Brain Res., 987(1):39-48), these results demonstrate that the activated NT drugs of the invention display unique pharmacodynamic properties with limited tolerance, allowing repeated or subchronic administrations at effective and safe dose levels.

Example 14

Antipyretic Effects of Activated NT Drugs of the Invention

In addition to eliciting a strong hypothermic effect when injected intravenously in naïve mice, we assessed the antipyretic effect of activated NT drugs of the invention in mice with yeast-induced hyperthermia. Briefly, rectal temperature of male NMRI mice was first measured 14 hours before the test using a rectal probe (Baseline 1, two independent measurements at a minimum of 5 min interval). Mice were then injected subcutaneously with either a yeast suspension (512 mg/kg), to induce a hyperthermic response, or hydroxypropylmethylcellulose (HPMC) in saline 0.9%. Fourteen hours later, rectal temperature of the mice was measured again (Baseline 2, two independent measurements at a minimum of 5 min interval) in order to assess the effect of yeast or HPMC injection on baseline temperature. Mice were then randomized and injected i.v. with the activated neurotensin molecule (compound XIV) or control (saline 0.9%), and rectal temperature was measured again 15, 30, 45, 60, 120 and 180 minutes later.

Control mice injected with the yeast suspension and receiving saline showed a typical 0.6-1° C. hyperthermia. The antipyretic effect of activated NT molecules of the invention was rated as its ability to reverse the induced hyperthermia. The results showed that compound XIV significantly reversed hyperthermia in mice as of 2 mg/kg eq. NT and with a rapid onset, with a maximal effect of −2.2° C. when compared to Baseline 2 of the same animals at 15 min post-injection or to time-matched animals treated with saline (FIG. 12). The antipyretic effect of compound XIV showed a dose-response relationship, with the possibility to further decrease body temperature to 4.7° C. at the dose level of 6 mg/kg eq. NT. This remarkable result shows that controlled normothermia or even moderate therapeutic hypothermia induced by the activated NT molecules of the invention could be used for neuroprotection in acute conditions associated with hyperthermia, such as focal cerebral ischemia, severe traumatic brain injury, ICH, viral, bacterial or parasitic infection and any acute condition where local inflammatory response may induce hyperthermia.

Example 15

Anticonvulsant, Neuroprotective and Anti-Neuroinflammatory Effects of Activated NT Drugs in a Mouse Model of Epilepsy and Excitotoxic Neuronal Death In this example, we evaluated the potential of activated NT drugs of the invention to promote neuroprotection following excitotoxicity associated with convulsions and seizures. More than any other cells, neurons are particularly sensitive to oxygen and glucose deprivation, a situation that induces massive release of glutamate, the main excitatory neurotransmitter of neurons. Excessive glutamate release by neurons induces, in turn, excessive neuronal activity, which causes rapid neuronal death and deleterious neuroinflammation. This process of excitotoxicity is common to all forms of brain ischemia, i.e., following sudden cardiac arrest (global cerebral ischemia), following stroke (focal ischemia) and neonatal ischemia. Excitotoxicity also occurs during seizures and in epilepsy and following brain and spinal cord trauma. In all cases, the rapid neuronal death observed in areas of the nervous system where neurons are particularly sensitive to excitotoxicity, such as the hippocampus, leads to irreversible neuronal damage, often with severe handicap or death. Seizures can also be associated with aberrant axonal sprouting, in particular of the mossy fibers of the hippocampus in the weeks following seizure onset.

In the present case, excitotoxicity was induced by subcutaneous (s.c.) injection of kainic acid (KA), a pro-convulsant agent known to induce a status epilepticus (SE) with excitotoxicity, neuroinflammation, and severe neuronal damage in the hippocampus that can be observed 3 to 7 days after KA administration, and with aberrant axonal sprouting of the dentate gyrus mossy fibers that can be observed at 7-8 weeks after KA administration. We tested the effect of compound XIV on i) epileptic activity (persistence of recurrent seizures), ii) neurodegeneration, neuroinflammation and the resulting brain tissue damage and iii) aberrant axonal sprouting of the dentate gyrus mossy fibers.

FVB/N adult male mice were injected with a single dose of KA (40-45 mg/kg s.c.) to generate mice with spontaneous recurrent seizures as a hallmark of SE. A negative control group of mice were administered saline 0.9% instead of KA and no further treatment ("SHAM", n=5). Thirty minutes after the onset of SE, mice received either an intravenous (tail vein) bolus injection of compound XIV at the dose of 4 mg/kg eq. NT (treatment group "SE+HT", n=5) or saline 0.9% (group "SE", n=5), or a high dose of diazepam (DZP) at 15 mg/kg), a potent anti-convulsive and anti-epileptic drug (positive control group "SE+DZP"). Body temperature was monitored before KA injection and then every 15 min during 6 hours thereafter, using a rectal probe. During this period, mice were assessed for the occurrence and severity of motor seizures. One week later, animals were sacrificed for histological assessment of neuronal cell death on coronal sections, the hippocampal formation being the main structure in the brain showing tissue damage in this model of excitotoxicity. Another group of animals with the same treatments was sacrificed 8 weeks for histological assessment of aberrant axonal sprouting of the dentate gyrus mossy fibers.

1) Effects of Activated NT Drug on Body Temperature and Seizure Intensity in Status Epilepticus: Compound XIV has Anticonvulsive Properties Administration of KA (40-45 mg/kg; s.c.) caused characteristic sequential behavioral changes. Immediately after being injected, all animals developed immobility (stage 1). Within 30 minutes after KA injection, automatisms with head nodding, forelimb clonus and circling behavior (stages 2-3) were observed. Then most animals progressed to intermittent (stage 4) followed by continuous (stage 5) rearing with forelimb clonus and falling behavior. Some mice displayed severe generalized tonic-clonic seizures (stage 6). Only animals attaining at least Racine stage 5 seizures were included in the study. The SE occurred around 2 hours after KA injection, was characterized by stage 5-6 seizures and often associated with hyperthermia (FIG. 13A). Compound XIV administered 30 min after SE onset (SE30) invariably led to transient hypothermia (FIG. 13A), which persisted at least 2 hrs. Mean decreases in body temperature (BT) of −2.5° C. and −3.6° C. were respectively recorded for SE30+ compound XIV animals as compared to SE animals (F=52.34; *P<0.001). This hypothermia was associated with a significant decrease of seizures in the SE30+ compound XIV group as compared with the SE group (F=823.96; * P<0,001; FIG. 13B). SE30+ compound XIV animals presented an average of stage 2 seizures or fewer during the rest of experiment. A subset of animals was administered i.p. a high dose of diazepam (DZP). As for SE30+ compound XIV animals, DZP-treated animals rapidly showed stage 1-2 seizures during the rest of the experiment and hypothermia was also observed in these animals (F=823.96; ***P<0,001; FIGS. 13A-B). No significant variations of BT or seizure intensity were observed when neurotensin NT(8-13) was administered 30 min after SE onset, as compared with SE animals. Thus, administration of compound XIV at the dose of 4 mg/kg eq. NT in SE animals (SE+HT group) induced a clear reduction or even suppression of motor seizures, demonstrating the potent anticonvulsant effect of the drug. This effect correlated with a −3 to −6° C. decrease in body temperature during ~2.5 hours.

2) Activated NT Drug Promotes Neuroprotection in the Hippocampus Following Status Epilepticus Using the anti-NeuN antibody and Fluoro-jade C that respectively label a neuronspecific nuclear protein and neuronal death, we observed a broad loss of CA1 and CA3 pyramidal cells as well as some dentate hilar neurons in the hippocampus of control SE animals (FIG. 14A, panel B), as compared to SHAM animals (FIG. 14A, panel A). Neurodegeneration observed in SE animals was significantly decreased when compound XIV or DZP was administered 30 min after SE onset (FIGS. 14A-B) but no changes were observed when NT(8-13) was administered. The results obtained for SE30+ compound XIV animals were significantly different from those observed in SE30+NT(8-13) groups but not different from those observed in SE30+DZP mice.

3) Activated NT Drug Attenuates Glial-Mediated Inflammatory Response in the Hippocampus Following Status Epilepticus SE-induced gliosis involved microglia and astroglial cell types. We used GFAP and Iba1 immunolabeling to estimate the effect of compound XIV on neuroinflammation. In SHAM animals, a basal labeling for GFAP and Iba1 was detected in the HF (FIG. 14A, panel D). In SE animals, a very strong activation of glial cells occurred in all hippocampal layers (FIG. 14, panels E, H). This inflammatory response was significantly decreased when compound XIV or DZP was administered 30 min after SE onset (FIG. 14, panels F, I), but no changes were observed when NT(8-13) was administered. The results obtained for SE30+ compound XIV animals were significantly different from those observed in SE30+NT(8-13) groups, but not different from those observed in SE30+DZP mice.

4) Activated NT Drug Reduces Mossy Fiber Spouting in the Hippocampus Following Status Epilepticus Sprouting of mossy fibers, the axons of dentate granule cells, is well-established in KA-treated mice and epilepsy in general. It has been proposed that this aberrant sprouting occurs in the inner molecular layer (IML) in response to hilar cell loss. To further investigate the neuroprotective effect of compound XIV, we evaluated the extent of mossy fiber sprouting 8 weeks after SE. Mossy fiber terminals are highly enriched in zinc ions and we used immunohistochemical labeling for the zinc vesicular transporter 3 (ZnT3) to detect mossy fiber sprouting, as illustrated in FIG. 15. In all SHAM animals, mossy fiber terminals are present in the hilus and stratum lucidum of the CA3 region and no terminals were observed in the IML of the DG (FIG. 15A, panels A, B; FIG. 15B). In SE animals, mossy fiber terminals were not only observed in the hilar and CA3 regions, as in SHAM mice, but also within the IML (FIG. 15A, panels C, D; FIG. 15B). In comparison with SE animals, the number of terminals innervating the IML was considerably reduced in animals administered with compound XIV (FIG. 15A, panels E, F; FIG. 15B) or DZP 30 min after SE onset, but not significantly changed when NT(8-13) was administered (FIG. 15B).

All these results clearly demonstrate that activated NT molecules of the invention not only represent an attractive approach to preventing brain tissue damage resulting from excitotoxic neuronal death and neuroinflammation, but also have the potential to inhibit motor seizures, presumably by reducing neuronal activity via hypothermia.

Example 16

Antinociceptive Effect of Tandem Activated NT Drugs

In order to evaluate the antinociceptive potential of activated NT drugs, compound XIV was tested in an experimental pain model in mice. The writhing test was used as a model of acute visceral pain to assess the effect of compound XIV after intravenous administration. Given that the time to maximal decrease in body temperature in mice receiving compound XIV was around 45 min post-injection, we assumed similar pharmacodynamic kinetics in this pain model. Mice first received intravenous (bolus) injection of compound XIV at increasing dose levels, followed 30 min thereafter by intraperitoneal injection of acetic acid 0.7% (10 mL/kg). In control mice, intraperitoneal injection of acetic acid produces characteristic and quantifiable abdominal stretches (elongation of the body and extension of forelimbs) as early as 2-3 minutes following injection and reaching a peak between 5 and 15 min following injection. This time window was therefore used to evaluate the number of abdominal stretches (writhes counted over 10 min observation) in mice administered with either saline or compound XIV at 0.5, 1 or 5 mg/kg eq. NT.

Compound XIV produced a significant and dose-dependent antinociceptive effect in this model, with no effect at 0.5 mg/kg eq. NT and a 50% and 64% reduction of the writhe count at 1 and 5 mg/kg eq. NT, respectively (FIG. 16).

In another preferred embodiment, the neurotensin polypeptide and activator group are coupled using a flexible linker selected from a polyG molecule, more preferably a G amino acid or a GGG tripeptide, or the linear aminohexanoic acid.

In another preferred embodiment, the neurotensin polypeptide and activator group are coupled using a cleavable disulfide bond.

In another preferred embodiment, the neurotensin polypeptide and activator group are coupled using a heterobifunctional crosslinker, more preferably the sulfo-EMCS reagent.

A list of most preferred activated neurotensin molecules of the invention is provided in the following Table A.

Detailed methods of producing activated neurotensin molecules of the invention are disclosed in the experimental section. In this respect, the invention also relates to a method for preparing an activated neurotensin molecule, comprising a step of covalent

The invention claimed is:
1. A compound selected from compounds I to XX as listed below, or pharmaceutically acceptable salts thereof:

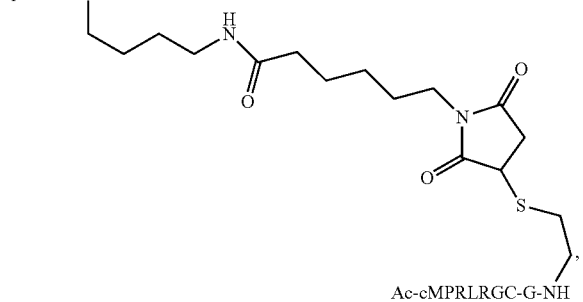
(I)

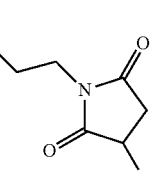
(II)

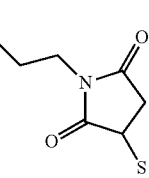
(III)

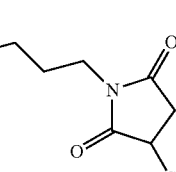
(IV)

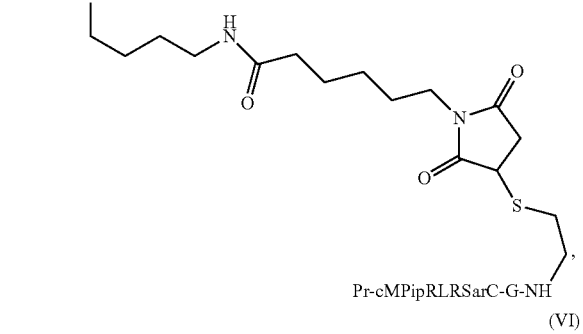
(V)

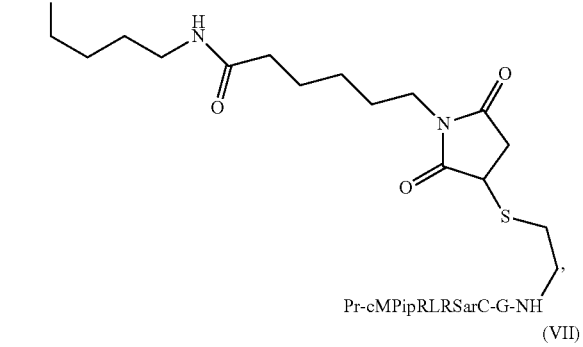
(VI)

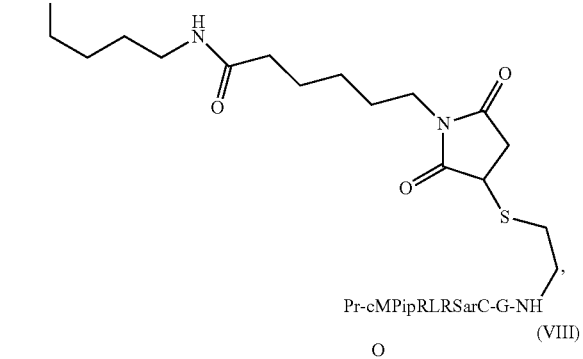
(VII)

(VIII)

Pr-cMPipRLRSarC-RRPYIL-OH (IX),
Pr-cMPipRLRSarC-GGG-KPRRPYIL-OH (X),
Pr-cMPipRLRSarC-Ahx-KPRRPYIL-OH (XI),
Pr-cMPipRLRSarC-Ahx-RRPYIL-OH (XII),
Pr-cMPipRLRSarC-PEG2-RRPYIL-OH (XIII),
Pr-cMPipRLRSarC-PEG6-RRPYIL-OH,
Pr-cMPipRLRSarC-RRPYTleL-OH (XV),
Pr-cMPipRLRSarC-KRPYTleL-OH (XVI),
Pr-cMPipRLRSarC-RKPYTleL-OH (XVII),
Pr-cMPipRLRSarC-RRPWTleL-OH (XVIII),
Pr-cMPipRLRSarC-KRPWTleL-OH (XIX), and
Pr-cMPipRLRSarPen-KRPYTleL-OH (XX).

2. A pharmaceutical composition comprising a compound as defined in claim 1 and a pharmaceutically acceptable carrier or excipient.

3. A method for reducing body temperature in a mammalian subject comprising administering to the subject a compound as defined in claim 1 or a composition thereof to said subject.

4. The method of claim 3, wherein hypothermia is induced in a mammalian subject following sudden cardiac arrest, or having a stroke, neonatal ischemia, heart surgery, traumatic head or spinal cord injury, seizures, pain or hyperthermia.

5. A method for protecting against or for reducing brain damage in a mammalian subject comprising administering to the subject a compound as defined in claim 1 or a composition thereof.

6. A method for reducing convulsions in a mammalian subject comprising administering to the subject a compound as defined in claim 1 or a composition thereof.

7. A method for reducing pain in a mammalian subject comprising administering to the subject a compound as defined in claim 1 or a composition thereof.

\* \* \* \* \*

UNITED STATES PATENT AND TRADEMARK OFFICE
CERTIFICATE OF CORRECTION

PATENT NO.       : 9,821,072 B2
APPLICATION NO.  : 15/111835
DATED            : November 21, 2017
INVENTOR(S)      : Guillaume Jacquot, Pascaline Lecorche and Michel Khrestchatisky It is certified that error appears in the above-identified patent and that said Letters Patent is hereby corrected as shown below:

In the Specification

Column 7,
Line 60, "[(D)-Orn9]NT(8-13)," should read --[(D)-Orn9]NT(8-13),--.

Column 10,
Line 31, "$G_45$" should read --$G_4S$--.

Column 14,
Line 54, compound IX, "Pr-cMPipRLRSarC-RRPYIL-OH" should read
--Pr-cMPipRLRSarC-RRPYIL-OH--.
Line 56, compound X, "Pr-cMPipRLRSarC-GGG-KPRRPYIL-OH" should read
--Pr-cMPipRLRSarC-GGG-KPRRPYIL-OH--.
Line 58, compound XI, "Pr-cMPipRLRSarC-Ahx-KPRRPYIL-OH" should read
--Pr-cMPipRLRSarC-Ahx-KPRRPYIL-OH--.
Line 60, compound XII, "Pr-cMPipRLRSarC-Ahx-RRPYIL-OH" should read
--Pr-cMPipRLRSarC-Ahx-RRPYIL-OH--.
Line 62, compound XIII, "Pr-cMPipRLRSarC-$PEG_2$-RRPYIL-OH" should read
--Pr-cMPipRLRSarC-$PEG_2$-RRPYIL-OH--.
Line 64, compound XIV, "Pr-cMPipRLRSarC-$PEG_6$-RRPYIL-OH" should read
--Pr-cMPipRLRSarC-$PEG_6$-RRPYIL-OH--.
Line 66, compound XV, "Pr-cMPipRLRSarC-RRPYTIeL-OH" should read
--Pr-cMPipRLRSarC-RRPYTleL-OH--.

Column 16,
Line 5, compound XVI, "Pr-cMPipRLRSarC-KRPYTIeL-OH" should read
--Pr-cMPipRLRSarC-KRPYTleL-OH--.
Line 7, compound XVII, "Pr-cMPipRLRSarC-RKPYTIeL-OH" should read
--Pr-cMPipRLRSarC-RKPYTleL-OH--.

Signed and Sealed this
Twenty-fifth Day of September, 2018

Andrei Iancu
*Director of the United States Patent and Trademark Office*

Line 9, compound XVIII, "Pr-cMPipRLRSarC-RRPWTIeL-OH" should read
--Pr-cMPipRLRSarC-RRPWTleL-OH--.
Line 11, compound XIX, "Pr-cMPipRLRSarC-KRPWTIeL-OH" should read
--Pr-cMPipRLRSarC-KRPWTleL-OH--.
Line 13, compound XX, "Pr-cMPipRLRSarPen-KRPYTIeL-OH" should read
--Pr-cMPipRLRSarPen-KRPYTleL-OH--.

Column 22,
Lines 60-61, "1-[Bis(dimethylamino)methylene]-1H-1,2,3-triazolo[4,5-13]pyridinium"
should read --1-[Bis(dimethylamino)methylene]-1H-1,2,3-triazolo[4,5-β]pyridinium--.

Column 33,
Line 8, "920.51. found" should read --920.51, found--.

Column 42,
Lines 1-20, "In another preferred embodiment, the neurotensin polypeptide and activator group are coupled using a flexible linker selected from a polyG molecule, more preferably a G amino acid or a GGG tripeptide, or the linear aminohexanoic acid.
    In another preferred embodiment, the neurotensin polypeptide and activator group are coupled using a cleavable disulfide bond.
    In another preferred embodiment, the neurotensin polypeptide and activator group are coupled using a heterobifunctional crosslinker, more preferably the sulfo-EMCS reagent.
    A list of most preferred activated neurotensin molecules of the invention is provided in the following Table A.
    Detailed methods of producing activated neurotensin molecules of the invention are disclosed in the Examples section. In this respect, the invention also relates to a method for preparing an activated neurotensin molecule, comprising a step of covalent" should read
--blank--.

In the Claims

Column 48,
Line 61, "Pr-cMPipRLRSarC-PEG6-RRPYIL-OH," should read
--Pr-cMPipRLRSarC-PEG6-RRPYIL-OH, (XIV),--.